US007998125B2

(12) United States Patent
Weston

(10) Patent No.: US 7,998,125 B2
(45) Date of Patent: Aug. 16, 2011

(54) HYPOBARIC CHAMBER TREATMENT SYSTEM

(75) Inventor: Richard Scott Weston, Carlsbad, CA (US)

(73) Assignee: BlueSky Medical Group Incorporated, Memphis, TN (US)

( * ) Notice: Subject to any disclaimer, the term of this patent is extended or adjusted under 35 U.S.C. 154(b) by 1372 days.

(21) Appl. No.: 11/132,549

(22) Filed: May 19, 2005

(65) Prior Publication Data

US 2005/0261615 A1    Nov. 24, 2005

Related U.S. Application Data

(60) Provisional application No. 60/573,653, filed on May 21, 2004.

(51) Int. Cl.
*A61M 1/00* (2006.01)
*E04G 11/04* (2006.01)
*E04B 1/34* (2006.01)

(52) U.S. Cl. ........ 604/317; 604/320; 604/321; 604/540; 604/543; 52/2.18

(58) Field of Classification Search ................... 604/317, 604/320, 321, 540, 543; 52/2.18
See application file for complete search history.

(56) References Cited

U.S. PATENT DOCUMENTS

| | | |
|---|---|---|
| 59,388 A | 11/1866 | Hadfield |
| 1,480,562 A | 1/1924 | Mock |
| 1,585,104 A | 5/1926 | Montgomery |
| 1,629,108 A | 5/1927 | Lake |

(Continued)

FOREIGN PATENT DOCUMENTS

CA    2049948 C    10/1990

(Continued)

OTHER PUBLICATIONS

3M Health Care, Controlling the Risk of Surgical Site Infections after Cardiovascular Procedures: The Importance of Providing a Sterile Surface, Brochure, St. Paul, MN and London, Ontario, Canada, 1997, 8 pages.

(Continued)

*Primary Examiner* — Tatyana Zalukaeva
*Assistant Examiner* — Ginger T Chapman
(74) *Attorney, Agent, or Firm* — Knobbe, Martens, Olson & Bear, LLP

(57) ABSTRACT

A reduced pressure treatment appliance is provided for enclosing and providing reduced pressure treatment to an object or a portion of an object. In some embodiments, the reduced pressure treatment appliance may be used to treat wounds and other conditions, such as lymphedema, varicose veins, venous insufficiency and stasis, and other infirmities. In other embodiments, the appliance may be used to provide reduced pressure (or vacuum) treatment for non-medical purposes. In some embodiments, the appliance comprises a flexible chamber and a collapsible frame that may be collapsed while the appliance is not in use. In yet other embodiments, the appliance also includes a vacuum system to supply reduced pressure to the volume within the chamber, a pressurized fluid system to inflate the collapsible frame, a drainage system to remove fluids from the appliance, and a treatment port and a forced entry treatment system to introduce fluids and other treatment instrumentalities into the volume within the chamber. In still other embodiments, the chamber is designed for use with distal extremital portions of a body. In further embodiments, the appliance also comprises a semipermeable liner positioned between the chamber and the portion of a body to be treated. Finally, methods are provided for using various embodiments of the appliance.

36 Claims, 7 Drawing Sheets

U.S. PATENT DOCUMENTS

| | | | |
|---|---|---|---|
| 1,732,310 A | 10/1929 | Naibert | |
| 1,863,534 A | 6/1932 | Odell | |
| 1,936,129 A | 11/1933 | Fisk | |
| 2,122,121 A | 6/1938 | Tillotson | |
| 2,280,915 A | 4/1942 | Johnson | |
| 2,318,888 A | 5/1943 | Sanders | |
| 2,366,799 A | 1/1945 | Luisada | |
| 2,367,690 A | 1/1945 | Purdy | |
| 2,385,683 A | 9/1945 | Buron | |
| 3,026,874 A | 11/1959 | Stevens | |
| 3,042,041 A | 7/1962 | Jascalevich | |
| 3,217,707 A | 11/1965 | Werding | |
| 3,238,937 A | 3/1966 | Stein | |
| 3,286,711 A | 11/1966 | MacLeod | |
| 3,315,665 A | 4/1967 | MacLeod | |
| 3,465,748 A * | 9/1969 | Kravchenko | 601/6 |
| 3,568,675 A | 3/1971 | Harvey | |
| 3,572,340 A | 3/1971 | Lloyd et al. | |
| 3,610,238 A | 10/1971 | Rich, Jr. | |
| 3,712,298 A | 1/1973 | Snowdon et al. | |
| 3,794,035 A | 2/1974 | Brenner | |
| 3,859,989 A * | 1/1975 | Spielberg | 601/11 |
| 3,874,387 A | 4/1975 | Barbieri | |
| 3,908,642 A | 9/1975 | Vinmont | |
| 3,938,540 A | 2/1976 | Holbrook et al. | |
| 3,961,625 A | 6/1976 | Dillon | |
| 3,988,793 A | 11/1976 | Abitbol | |
| RE29,319 E | 7/1977 | Nordby et al. | |
| 4,102,342 A | 7/1978 | Akiyama et al. | |
| 4,224,945 A | 9/1980 | Cohen | |
| 4,250,882 A | 2/1981 | Adair | |
| 4,256,109 A | 3/1981 | Nichols | |
| 4,382,441 A | 5/1983 | Svedman | |
| 4,392,858 A * | 7/1983 | George et al. | 604/133 |
| 4,396,023 A | 8/1983 | Anderson | |
| 4,421,109 A * | 12/1983 | Thornton | 601/35 |
| 4,432,354 A * | 2/1984 | Lasley | 601/43 |
| 4,444,548 A | 4/1984 | Anderson et al. | |
| 4,459,139 A | 7/1984 | vonReis et al. | |
| 4,465,485 A | 8/1984 | Kashmer et al. | |
| 4,469,092 A | 9/1984 | Marshall et al. | |
| 4,525,166 A | 6/1985 | Leclerc | |
| 4,624,656 A * | 11/1986 | Clark et al. | 604/23 |
| 4,691,695 A * | 9/1987 | Birk et al. | 601/6 |
| 4,710,165 A | 12/1987 | McNeil et al. | |
| 4,738,249 A * | 4/1988 | Linman et al. | 601/152 |
| 4,740,202 A * | 4/1988 | Stacey et al. | 604/119 |
| 4,768,501 A | 9/1988 | George | |
| 4,772,259 A | 9/1988 | Frech et al. | |
| 4,790,833 A | 12/1988 | Schmidt | |
| 4,820,284 A | 4/1989 | Hauri | |
| 4,828,546 A | 5/1989 | McNeil et al. | |
| 4,921,488 A | 5/1990 | Maitz et al. | |
| 4,950,483 A | 8/1990 | Ksander | |
| 4,969,880 A | 11/1990 | Zamierowski | |
| 5,000,164 A * | 3/1991 | Cooper | 601/11 |
| 5,100,376 A * | 3/1992 | Blake, III | 604/6.1 |
| 5,100,396 A | 3/1992 | Zamierowski | |
| 5,149,331 A | 9/1992 | Ferdman et al. | |
| 5,152,757 A | 10/1992 | Eriksson | |
| 5,228,431 A | 7/1993 | Giarretto | |
| 5,243,968 A | 9/1993 | Byun | |
| 5,261,893 A | 11/1993 | Zamierowski | |
| 5,307,791 A | 5/1994 | Senoue et al. | |
| 5,312,385 A * | 5/1994 | Greco | 604/356 |
| 5,362,543 A | 11/1994 | Nickerson | |
| 5,398,678 A * | 3/1995 | Gamow | 128/205.26 |
| 5,419,768 A | 5/1995 | Kayser | |
| 5,425,742 A * | 6/1995 | Joy | 606/203 |
| 5,462,514 A | 10/1995 | Harris | |
| 5,489,280 A | 2/1996 | Russell | |
| 5,514,166 A | 5/1996 | Silver et al. | |
| 5,549,584 A | 8/1996 | Gross | |
| 5,577,994 A | 11/1996 | Celik | |
| 5,609,163 A * | 3/1997 | Beard | 128/846 |
| 5,624,419 A * | 4/1997 | Ersek et al. | 604/355 |
| 5,636,643 A | 6/1997 | Argenta | |
| 5,645,081 A | 7/1997 | Argenta | |
| 5,688,225 A | 11/1997 | Walker | |
| 5,688,236 A * | 11/1997 | Gragg | 604/23 |
| 5,701,917 A | 12/1997 | Khouri | |
| 5,716,411 A | 2/1998 | Orgill et al. | |
| 5,769,725 A * | 6/1998 | Ogden et al. | 472/59 |
| 5,827,246 A | 10/1998 | Bowen | |
| 5,830,496 A | 11/1998 | Freeman | |
| 5,865,772 A | 2/1999 | George | |
| 5,893,368 A | 4/1999 | Sugerman | |
| 5,938,626 A | 8/1999 | Sugerman | |
| 5,970,266 A | 10/1999 | Takato | |
| 6,045,541 A | 4/2000 | Matsumoto | |
| 6,113,548 A | 9/2000 | deBoisblanc et al. | |
| 6,135,116 A | 10/2000 | Vogel et al. | |
| D434,150 S | 11/2000 | Tumey | |
| 6,142,982 A | 11/2000 | Hunt | |
| 6,176,307 B1 | 1/2001 | Danos et al. | |
| 6,287,521 B1 | 9/2001 | Quay et al. | |
| 6,321,746 B1 * | 11/2001 | Schneider et al. | 128/202.12 |
| 6,371,976 B1 | 4/2002 | Vrzalik et al. | |
| 6,398,767 B1 | 6/2002 | Fleischmann | |
| 6,402,724 B1 | 6/2002 | Smith et al. | |
| 6,458,109 B1 | 10/2002 | Henley et al. | |
| 6,471,685 B1 | 10/2002 | Johnson | |
| 6,547,756 B1 | 4/2003 | Greter et al. | |
| 6,566,833 B2 | 5/2003 | Bartlett | |
| 6,595,949 B1 | 7/2003 | Shapiro | |
| 6,673,028 B1 | 1/2004 | Argenta et al. | |
| 6,685,681 B2 | 2/2004 | Lockwood et al. | |
| 6,695,823 B1 | 2/2004 | Lina et al. | |
| 6,904,631 B2 | 6/2005 | Vrzalik et al. | |
| 6,936,037 B2 | 8/2005 | Bubb et al. | |
| 6,951,553 B2 | 10/2005 | Bubb et al. | |
| 6,979,324 B2 | 12/2005 | Bybordi et al. | |
| 6,988,423 B2 | 1/2006 | Bolam et al. | |
| 6,994,702 B1 | 2/2006 | Johnson | |
| 7,004,915 B2 | 2/2006 | Boynton et al. | |
| 7,070,584 B2 | 7/2006 | Johnson et al. | |
| 7,077,832 B2 | 7/2006 | Fleischmann | |
| 7,108,683 B2 | 9/2006 | Zamierowski | |
| 7,117,869 B2 | 10/2006 | Heaton et al. | |
| 7,128,735 B2 | 10/2006 | Weston | |
| 7,144,390 B1 | 12/2006 | Hannigan et al. | |
| 7,198,046 B1 | 4/2007 | Argenta et al. | |
| 7,214,202 B1 | 5/2007 | Vogel et al. | |
| 7,216,651 B2 * | 5/2007 | Argenta et al. | 128/897 |
| 7,235,066 B1 | 6/2007 | Narini et al. | |
| 7,279,612 B1 | 10/2007 | Heaton et al. | |
| 7,381,859 B2 | 6/2008 | Hunt et al. | |
| 7,494,482 B2 | 2/2009 | Orgill et al. | |
| 7,776,028 B2 * | 8/2010 | Miller et al. | 604/543 |
| 2001/0029956 A1 | 10/2001 | Argenta et al. | |
| 2001/0043943 A1 * | 11/2001 | Coffey | 424/447 |
| 2002/0040687 A1 | 4/2002 | van der Lely et al. | |
| 2002/0065494 A1 | 5/2002 | Lockwood et al. | |
| 2002/0068913 A1 | 6/2002 | Fleischmann | |
| 2002/0115952 A1 | 8/2002 | Johnson | |
| 2002/0143286 A1 | 10/2002 | Tumey | |
| 2002/0161346 A1 | 10/2002 | Lockwood et al. | |
| 2002/0183702 A1 * | 12/2002 | Henley et al. | 604/305 |
| 2002/0198503 A1 | 12/2002 | Risk | |
| 2002/0198504 A1 | 12/2002 | Risk | |
| 2003/0040687 A1 | 2/2003 | Boynton et al. | |
| 2003/0050594 A1 | 3/2003 | Zamierowski | |
| 2003/0108587 A1 | 6/2003 | Orgill et al. | |
| 2003/0125646 A1 | 7/2003 | Whitlock | |
| 2003/0212357 A1 | 11/2003 | Pace | |
| 2003/0216672 A1 | 11/2003 | Rastegar et al. | |
| 2003/0225347 A1 | 12/2003 | Argenta et al. | |
| 2004/0050411 A1 * | 3/2004 | Lawrence | 135/128 |
| 2004/0073151 A1 | 4/2004 | Weston | |
| 2005/0203452 A1 | 9/2005 | Weston | |
| 2005/0222527 A1 * | 10/2005 | Miller et al. | 602/1 |
| 2005/0222528 A1 | 10/2005 | Weston | |
| 2005/0222544 A1 | 10/2005 | Weston | |
| 2005/0261642 A1 | 11/2005 | Weston | |
| 2005/0261643 A1 | 11/2005 | Bybordi et al. | |
| 2007/0167926 A1 | 7/2007 | Blott et al. | |
| 2007/0239139 A1 | 10/2007 | Weston et al. | |

| | | |
|---|---|---|
| 2007/0265585 A1 | 11/2007 | Joshi |
| 2008/0132819 A1 | 6/2008 | Radl et al. |
| 2010/0160880 A1 | 6/2010 | Weston |

FOREIGN PATENT DOCUMENTS

| | | |
|---|---|---|
| CA | 2369000 A1 | 10/1990 |
| CA | 2103033 C | 11/1992 |
| CA | 2414393 A1 | 11/1992 |
| CA | 2115951 A1 | 8/1994 |
| CA | 2157772 C | 9/1995 |
| CA | 2198243 A1 | 2/1996 |
| CA | 2237606 A1 | 5/1997 |
| CA | 2238413 A1 | 5/1997 |
| CA | 2551340 A1 | 5/1997 |
| CA | 2303085 A1 | 3/1999 |
| CA | 2471780 A1 | 3/1999 |
| CA | 2347115 A1 | 4/2000 |
| CA | 2369024 A1 | 10/2000 |
| CA | 2390513 A1 | 5/2001 |
| CA | 2408305 A1 | 11/2001 |
| CA | 2351342 A1 | 6/2002 |
| CA | 2432293 A1 | 2/2003 |
| CA | 2368085 C | 5/2006 |
| DE | 3935818 | 10/1990 |
| EP | 1 897 569 B1 | 8/2002 |
| GB | 114754 | 4/1918 |
| GB | 2195225 | 4/1988 |
| GB | 2195255 | 4/1988 |
| RU | 240188 | 3/1969 |
| WO | WO 87/04626 | 8/1987 |
| WO | WO 90/11795 | 10/1990 |
| WO | WO 2006/114637 | 11/2006 |
| WO | WO 2007/087809 | 8/2007 |

OTHER PUBLICATIONS

A Sensational Medical Discovery, Brit. Journal Nursing, Jul. 15, 1911, p. 42.
Agarwala, S., et al., Use of Mini-Vacuum Drains in Small Surgical Wounds, Plastic and Reconstructive Surgery, Apr. 1998, 101(5), pp. 1421-1422 (Correspondence).
Agrama, H.M., Functional Longevity of Intraperiotoneal Drains, Amer. Journ. of Surg., Sep. 1976, 132, pp. 418-421.
Alper, J.C., et al., An Effective Dressing for a Large, Draining Abdominal wound, RN, Dec. 1988, pp. 24-25.
Alper, J.C., et al., Moist Wound Healing under a Vapor Permeable Membrane, Journ. of Amer. Acad. of Derm., Mar. 1983, 8(3), pp. 347-353.
Antonic, "Experience with the Use of Vacuum Therapy," Vacusac, Timocki Medicinski Glasnik, Year XII, Zajecar, 1987, No. 1, pp. 77-82.
Article Excerpt, Lancet, Jun. 14, 1952, pp. 1175-1176.
Article Excerpt: Part III. Resolving Selected Clinical Dilemmas, pp. 17-20.
Ashrafov, A.A. and K.G. Ibishov, An Experimental and Clinical Validation for the Use of a Collagen Sponge for Treating the Suppurative-Inflammatory Complications of Wound Healing in Emergency Abdominal Surgery, PubMed, Abs. Downloaded from Internet, Apr. 24, 2006, 1 page.
Assessing the Patient with a Fistula or Draining Wounds, Nursing, Jun. 1980, pp. 49-51.
Aubrey, D.A., et al., Treatment of the Perineal Wound after Proctectomy by Intermittent Irrigation, Arch. Surg., Oct. 1984, 119, pp. 1141-1144.
Avocat, C. et al., Nouvelle Presentation de Materiel Pour Drainage de Redon et Jost, La Nouvelle Press Medicale, Jun. 26, 1976, 5(6), pp. 1644-1645 (in French).
Ayoub, M.H. and G. C. Bennet, A Study of Cutaneous and Intracompartmental Limb Pressures Associated with the Combined Use of Tourniquets and Plaster Casts, Abs., Proc. and Reports of Univ., Colleges, Councils, Assoc., and Societies, 68-B:3, May 1986, p. 497.
Bagautdinov, "Variant of External Vacuum Aspiration in the Treatment of Purulent Diseases of Soft Tissues," Current Problems in Modern Clinical Surgery, 1986, 4 pages.

Baldwin, J.F., Ed., The Columbus Medical Journal, Columbus, Ohio, 1887, vol. 5, p. 561.
Barbul, A., et al., Eds., Clinical and Experimental Approaches to Dermal and Epidermal Repair, Normal and Chronic Wounds, Progress in Clin. and Biol. Res., vol. 365, Proc. of the 3rd Intnl. Symp. on Tissue Repair, Miami, FL, Jan. 10-14, 1990, Abs.
Bar-El, Y. et al., Potentially dangerous Negative Intrapleural pressures Generated by Ordinary Pleural Drainage Systems, Chest, Feb. 2001, 119(2), pp. 511-514.
Barker, D.E., et al., Vacuum Pack Technique of Temporary Abdominal Closure: A 7-Year Experience with 112 Patients, Journ. of Trauma: Injury and Critical Care, Feb. 2000, 4892), pp. 201-207.
Bascom, J., Pilonidal Sinus, Current Therapy in Colon and Rectal Surgery, 1990, pp. 1-8.
Benjamin, P.J., Faeculent Peritonitis: A Complication of Vacuum Drainage, Br. J. Surg., 1980, 67, pp. 453-454.
Berman and Fabiano, Closed Suction Drainage, Orthopedics, Mar. 1990, 13(3), pp. 310-314.
Berman, A. T., et al., Comparison Between Intermittent (Spring-Loaded) and Continuous Closed Suction Drainage of Orthopedic Wounds: A Controlled Clinical Trial, Orthopedics, Mar. 1990, 13(3), 9 pgs.
Besst, J.A., Wound Healing—Intraoperative Factors, Nursing Clinics of North America, Dec. 1979, 14(4), pp. 701-712.
Bier, A., Hyperemia as a Therapeutic Agent, Ed. Dr. Gustavus M. Blech, A. Robertson & Co., Chicago 1905. (the entire reference has been submitted, but pp. 74-85 may be the most relevant).
Birdsell, D.C., et al., The Theoretically Ideal Donor Site Dressing, Gadgetry, Div. of Plastic Surgery, Foothills, Hospital, Calgary, Canada, pp. 535-537.
Bischoff, et al., Vacuum-Sealing Fixation of Mesh Grafts, Euro. Journ. Plast. Surg., Jul. 2003, 26(4), pp. 189-190, Abs. Downloaded from internet Apr. 6, 2006.
Bonnema, J., et al., A Prospective Randomized Trial of High Versus Low Vacuum Drainage after Axillary Dissection for Breast Cancer, Amer. Journ. Surg., Feb. 1997, 173, pp. 76-79.
Boretos, "Cellular Polymers for Medical Use: The Vital Role of Porosity and Permeability," Cellular Polymers, 1984, vol. 3, pp. 345-358.
Britton, B.J., et al., A Comparison Between Disposable and Non-Disposable Suction Drainage Units: A Report of a Controlled Trial, Br. J. Surg. 1979, 66, pp. 279-280.
Broader, J.H., et al., Management of the Pelvic Space after Proctectomy, Br. J. Surg., 1974, 62, pp. 94-97.
Bruno, P., The Nature of Wound Healing: Implications for Nursing Practice, Nursing Clinics of North American, Dec. 1979, 14(4), pp. 667-682.
Bucalo et al. "Inhibition of Cell Proliferation by Chronic Wound Fluid." Wound Repair and Regeneration. Miami, 1993. pp. 181-186.
Burdette-Taylor, S.R., Use of the Versatile One (V1) for Closed Suction Drainage to Stimulate Closure in Chronic Wounds in Home Care, Case Study Presentation, 2003, 2 pgs.
Bush, G.K., What is a Counter Irritant? Name Any That You Know and the Method of their Application, Brit. Journ. Nurs., Oct. 1927, p. 232.
Calhoun, P. and K. Kenney, Pouching Management of Patients with Open abdomen, Eviscerations and Bowel Fistulas, Case Studies, Univ. of Miami/Jackson Memorial Medical Center, 1 page.
Candiani, P., et al., Repair of a Recurrent Urethrovaginal Fistula with an Island Bulbocavernous Musculocutaneous Flap, Plastic and Reconstructive Surgery, Dec. 1993, pp. 1393-1394.
Chardack et al., "Experimental Studies on Synthetic Substitutes for Skin and Their Use in the Treatment of Burns," Annals of Surgery, 1962, vol. 155, No. 1, pp. 127-139.
Carroll, P.L., The Principles of Vacuum and its Use in the Hospital Environment, 2nd Ed., 1986, 30pgs.
Chart: Influence of Wound Closure on Healing of Perineal Wound after Abdominoperineal Resection or Total Proctocolectomy, excerpt faxed Jan. 23, 2006, 1 page.
Chua Patel, C.T., et al., Vacuum-Assisted Closure, AJN, Dec. 2000, 100(12), pp. 45-49.
Cobb, J.P., Why Use Drains?, Br. J. Bone Joint Surg., Nov. 1990, 72-B(6), pp. 993-995.

Cooper, D.M., Optimizing Wound Healing, Nursing Clinics of North America, Mar. 1990, 25(1), pp. 163-179.

Cooper, D.M., Postsurgical Nursing Intervention as an Adjunct to Wound Healing, Nursing Clinics of North America, Dec. 1979, 14(4), pp. 713-726.

Cooper, S.M. and E. Young, Topical Negative Pressure, Commentary, International Journal of Dermatology 2000, 39, pp. 896-898.

Costunchenok, B.M., et al., Effect of Vacuum on Surgical Purulent Wounds, Vestnik Chirurgia 1986, September, pp. 18-20 (in Russian with English translation).

Cotton, P.B., et al., Early Endoscopy of Oesophagus, Stomach, and Duodenal Bulb in patients with Haematemesis and Melaena, Br. Med. Journ., Jun. 1973, 2, pp. 505-509.

Crisp, W.J. and A. Gunn, Granuflex Dressings for Closed Surgical Wounds Combined with Suction Drainage, Annals of the Royal College of Surgeons of England, 1990, 72, p. 76.

Cucuroos, Y.C., Vacuum Drainage of Post Operative Wounds, Kiev Army Hospital, Dept. of Hospital Surgery, Kiev medical University, pp. 64-65 (in Russian with English translation).

Curtin, L.L., Wound Management: care and Cost—an Overview, Nursing Management, Feb. 1984, 15, pp. 22-25.

Davidov, Y.A., et al. Justifying the Usage of Force Early Secondary Sutures in treatment of Purulent Wounds by the Vacuum Therapy, Vestnik Chirurgia 1990, March Edition, pp. 126-129 (in Russian with English translation).

Davidov, Y.A., et al., Concept of Clinico-Biological Management of Wound Process in Treatment of Purulent Wounds with the Help of Vacuum Therapy, Vestnik Chirurgia 1991, February Edition, pp. 132-135 (English translation).

Davidov et al. Pathogenic Mechanism of the Effect of Vacuum Therapy on the Course of the Wound Process Dec. 1990, pp. 42-47.

Davis, J.C. and T.K. Hunt, Eds., Problem Wounds: The Role of Oxygen, Chap. 1, Infection and Oxygen, 1988, pp. 1-15.

Dilmaghani et al., "A Method for Closed Irrigation and Suction Therapy in Deep Wound Infections," Journal of Bone and Joint Surgery, 1969, vol. 51-A, No. 2, pp. 323-342.

Doillon, C.J., et al., Collagen-Based Wound Dressings: Control of the Pore Structure and Morphology, Journal of Biomedical Materials Research, Sep. 13, 2004, 20(8), pp. 1219-1228. Abs. Downloaded from Internet http://www3.interscience.wiley.com, Apr. 28, 2006.

Domkowski, P.W., et al., Evaluation of Vacuum-Assisted Closure in the Treatment of Poststernotomy Mediastinitis, Journ. of Thorac. and Cardiovascular Surg., Aug. 2003, 126(2), pp. 386-390.

Doss, Mirko, et al., Vacuum-Assisted Suction Drainage Versus Conventional Treatment in the Management of Poststernotomy Osteomyelitis, Euro. Journ. Cardio-Thoracic. Surg. 22 ((2002) 934-938.

Draper, J., Make the Dressing Fit the Wound, Nursing Times, Oct. 9, 1985, pp. 32-35.

Dunbar, J.M., State What You Have Learned Recently on the Up-to-Date Care of Wounds, Brit. Journ. Nurs., Dec. 1941, p. 200.

Dunlop, M.G, et al. Vacuum Drainage of Groin Wounds after Vascular Surgery: A Controled Trial, Br. J. Surg., May 1990, 77, pp. 562-563.

Eaglstein, W.H., et al., Wound Dressings: Current and Future, Clin. and Exper. Approaches to Dermal and Epidermal Repair: Normal and Chronic Wounds, 1991, pp. 257-265.

ECRI, Target Report, Negative Pressure Wound Therapy for Chronic Wounds, Jan. 24, 2006, pp. 1-7, Downloaded from internet, http://www.target.ecri.org/summary/detail.aspx?dox_id=1155.

Eisenbud, D.E., Modern Wound Management, Anadem Publishing, Chap. 16, pp. 109-116.

Ellingwood, F., Ellingwood's Therapeutist, Jun. 14, 1908, 2(6), pp. 32-33.

Elwood, E.T., and D.G. Bolitho, Negative-Pressure Dressings in the Treatment of Hidradenitis Suppurative, Annals of Plastic Surgery, Jan. 2001, 46(1), pp. 49-51.

Engdahl, O. and J. Boe, Quantification of Aspirated Air Volume reduces Treatment Time in Pneumothorax, Eur. Respir, J., 1990, 3, pp. 649-652.

Engdahl, O., et al., Treatment of Pneumothorax: Application of a Technique which Quantifies Air Flow Through the Chest Drain, Adv. in Therapy, May/Jun. 1988, 5(3), pp. 47-54.

Erichsen, J.E., Science and Art of Surgery, London: Longmans, Green, and Co., 1895, vol. 1, pp. 258-259, and p. 289.

Fabian, T.S., The Evaluation of Subatmospheric Pressure and Hyperbaric Oxygen in Ischemic Full-Thickness Wound Healing, Ischemic Full-Thickness Wound Healing, Dec. 2000, 66(12), pp. 1136-1143.

Fay, M.F., Drainage Systems: Their Role in Wound Healing, AORN Journal, Sep. 1987, 46(3), pp. 442-455.

Fellin, R., Managing Decubitus Ulcers, Nursing Management, Feb. 1984, pp. 29-30.

Fingerhut, A., et al., Passive vs. Closed Suction drainage after Perineal Wound Closure Following Abdominoperineal Rectal Excision for Carcinoma, Dis Colon Rectum, Sep. 1995, pp. 926-932.

Firlit, C.F. and J.R. Canning, Surgical Wound Drainage: A Simple Device for Collection, Journ. of Urology, Aug. 1972, 108, p. 327.

Fisher, Jack, and R. W. Bert, Jr., A Technique for Skin Grafting Around Abdominal Wall Fistulas, Annals of Plastic Surgery, 11:6, Dec. 1983, pp. 563-564.

Flanagan, et al., Optional Sump: Novel Use of Triple Lumen Closed Drainage System, Anz. J. Surg., Nov. 2002, 72(11), pp. 806-807, Abs. Downloaded from internet Nov. 30,2003.

Fleck, C.A., When Negative is Positive: A Review of Negative Pressure Wound therapy, Wound Care, Mar./Apr. 2004, pp. 20-25.

Fleischmann, W. Wund Forum Spezial, "Vakuumversiegelung zur Behandlung von Problemwunden" (with English translation: Vacuum Sealing for Treatment of Problematical Wounds), IHW '94, 6 pages.

Fleischmann, Vacuum sealing: indication, technique, and results, European Journal of Orthopaedic Surgery & Traumatology (1995), 5 pages.

Flynn, M.E. and D.T. Rovee, Wound Healing Mechanisms, Amer. Journ. of Nursing, Oct. 1982, pp. 1544-1556.

Fox, J.W. and G.T. Golden, The Use of Drains in Subcutaneous Surgical Procedures, Amer. Journ. of Surg, Nov. 1976, 132, pp. 673-674.

Geiger Jones, E., et al., Management of an Iliostomy and Mucous Fistula Located in a Dehisced Wound in a Patient with Morbid Obesity, J. WOCN, Nov. 2003, 30(6), pp. 351-356.

Gill, P., What is a Counter-Irritant? Name Three and the Method of Applying them, Brit. Journ. Nurs., Jun. 1934, p. 142.

Goddard, L., Inflammation: Its Cause and Treatment, Brit. Journ. Nurs., Jan. 1944, 1 page.

GOMCO Suction Equipment & Accessories Guide, Catalog, Apr. 2006, pp. 1-18.

Gouttefangeas, C. et al., Functional T Lymphocytes Infiltrate Implanted Polyvinyl Alcohol Foams During Surgical Wound Closure Therapy, Clin. Exp. Immunol. 2001, 124, pp. 398-405.

Grabowski, S., Leczenie ran z zastosowaniem posicśnienia (wg Redona I Josta), II Klinik Xhieuefxnej AM w Warszawie; klerownik: Prof. Dr. Z. Lapinski, No. 1, pp. 19-21 (in Polish).

Grishdevich, V. and N. Ostrovsky, Postburn Facial Resurfacing with a Split Ascending Neck Flap, Plastic and Reconstructive Surgery, Dec. 1993, pp. 1384-1391.

Grobmyer, et al., High-Pressure Gradients Generated by Closed-Suction Surgical Drainage Systems, Surg. Infect. (Larchmt), Autumn 2002, 3(3), pp. 245-249, Abs., Downloaded Nov. 30, 2003.

Grover, R. and R. Sanders, Recent Advances: Plastic Surgery, Clinical Review, BMJ, Aug. 8, 1998, 317, pp. 397-400.

Gupta, S., Ed., Guidelines for Managing pressure Ulcers with Negative Pressure Wound Therapy, Advances in Skin & Wound Care Suppl., Nov./Dec. 2004, 17(2), pp. 1-16.

Gupta, S., Guidelines for Managing: Pressure Ulcers with Negative Pressure Wound Therapy, Downloaded from internet http://proquest.umi.com on Feb. 3, 2006, 19 pages.

Gwan-Nulla, D.N. and R.S. Casal, Toxic Shock Syndrome Associated with the Use of the Vacuum-Assisted Closure Device, Ann. Plast. Surg., Nov. 2001, 47(5), pp. 552-554.

Hallstrom, B.R. and J.F. Steele, Postoperative Course after Total Hip Arthroplasty: Wound Drainage versus No Drainage, Orthopaedic Review, Jul. 1992, pp. 847-851.

Hanbok för Hälso-Och Sjukvårdsarbete Lokal Anvisning för Landstinget Sörmland, Jan. 2001, 7 pgs, (in Swedish), Downloaded from Internet http://www.landstinget.sormland.se, Aug. 14, 2001.

Harkiss, K., Cheaper in the Long Run, Community Outlook, Aug. 1985, pp. 19-22.

Hartz, R.S., et al., Healing of the Perineal Wound, Arch. Surg., Apr. 1980, 115, pp. 471-474.

Harvard Pilgrim Health Care, Technology Assessment Policy, TA 6.29 Negative Pressure Wound therapy for Wound Healing, Dec. 2004, pp. 1-6.

Hay, J., et al., Management of the Pelvic Space With or Without Omentoplasty after Abdominoperineal Resection for Carcinoma of the Rectum: a Prospective Multicenter Study, Eur. J. Surg, 1997, Abs, 1 page.

Higgins, S., The Effectiveness of Vacuum Assisted Closure (VAC) in Wound Healing, Centre for Clinical Effectiveness, Monash Medical Centre, Clayton VIC Australia, Dec. 2003, pp. 1-16.

Hilsabeck, J.R., The Presacral Space as a Collector of Fluid Accumulations Following Rectal Anastomosis: Tolerance of Rectal Anastomosis to Closed Suction Pelvic Drainage, Amer. Soc. of Colon and Rectal Surgeons, Oct., 25(7), pp. 680-684.

Hilton, P., Surgical Wound Drainage: A Survey of Practices among Gynaecologists in the British Isles, Br. Journ. of Obstetrics and Gynaecology, Oct. 1988, 95, pp. 1063-1069.

Hollis, H.W. and M.R. Troy, A Practical Approach to Wound care in patients with Complex Enterocutaneous Fistulas, Surg., Gyn. & Obs., Aug. 1985, 161, pp. 179-181.

Hugh, T.B., Abdominal Wound Drainage, Med. Journ. of Australia, May 4, 1987, 146, p. 505 (Correspondence).

Hulten, L., et al., Primary Closure of Perineal Wound after Proctocolectomy or Rectal Excision, Acta Chir. Scand., 1971, 137, pp. 467-469.

Hunt, T.K. and J.E. Dunphy, Eds., Fundamentals of Wound Management, Appleton-Century-Crofts/New York, pp. 416-447.

Ilizarov, G.A., The Tension-Stress Effect on the Genesis and Growth of Tissues: Part II., Clinical Orthopaedics and Related Research, Feb. 1989, 239, pp. 263-283.

Izmailov, S.G., et al., Device for Treatment of wounds and Abdominal Cavity, Contents, Surg. No. 8 1997, Downloaded from internet http://www.mediasphera.ru/surgery/97/8/e8-97ref.htm, 1 page.

Izmailov, S.G., The Treatment of Eventrations with a Special Apparatus, Abstracts, Surg. No. 1 1997, Downloaded from internet, http://www.mediasphera.ru/surgery/97/1/el-97ref.htm, 1 page.

International Standard ISO 10079-1, First Edition, May 15, 1991, 2 pages.

Jeter, K., Closed Suction Wound Drainage System, J. WOCN, Mar./Apr. 2004, 51 (correspondence) 1 page.

Jeter, Katheerine F. ET, Managing Draining Wounds and Fistulae: New and Established Methods, Chronic Wound Care, Chapter 27, pp. 240-246.

Johnson, F.E., An Improved Technique for Skin Graft Placement using a Suction Drain, Surgery, Gynecology & Obstetrics, Dec. 1984, 159(6), pp. 584-585.

Kazan Medical Institute Doctors, A Gadget to Bring the Wound Edges Close, pp. 78-79 (in Russian with English translation). Aug. 20, 1985.

KCI, Inc., If It's Not V.A.C. Therapy, It's Not Negative Pressure Wound Therapy, KCI Brochure, Jan. 2005, pp. 1-5.

KCI, Inc., Introducing the V.A.C. GranuFoam Silver Dressing, Advertisement Flyer in 2 pgs.

KCI, Inc., The V.A.C. System, 2000-2001, Brochure, 2 pgs.

KCI, Inc., Vacuum Assisted Closure (VAC) from Wound Healing, Evidence Note 5, NHS Quality Improvement Scotland, Nov. 2003, 1 page.

Keen, W.W., Ed., Surgery, Its Principles and Practice, 1919, W. B. Saunders Company, p. 56, excerpt.

Keith, C.F., Wound management Following Head and Neck Surgery, Nursing Clinics of North America, Dec. 1979, 14(4) pp. 761-779.

Kennard, H.W., Bier's Hyperaemia, Brit. Journ. Nurs., Mar. 20, 1909, p. 223.

Khil'Kin, A.M., Use of a Collagen Hemostatic Sponge for the Experimental Closing of the Surface of a Liver Wound (article in Russian), Citation Downloaded from internet http://www.ncbi.nlm.nih.gov Apr. 24, 2006, 1 page.

Kiemele, L.J., et al., Catheter-Based Negative Pressure Wound Therapy: A New Paradigm of Care, Nursing Home Wound Care consultative Service, Mayo Clinic, Rochester, MN, 2 pages.

Kim, S.H., et al., Wangensteen Suction Drainage, apparatus in Neurosurgical Practice, Dept. of Neurosurgery, Yonsei University of College of Medicine, Seoul, Korea, 1975, pp. 159-160, Abs. (in Korean and Abstract in English).

Kloth, L.C. and J.M. McCulloch, Wound Healing Alternatives in Management, 3rd Ed., Chap. 10, pp. 339-352.

Kordasiewicz, L.M., Abdominal Wound with a Fistula and Large Amount of Drainage Status after Incarcerate Hernia Repair, J. WOCN, May/Jun. 2004, 31(3), pp. 150-153.

Kremlin Papers, A Collection of Published Studies Complementing the Research and Innovation of Wound Care, from Vestnik Khirurgii, BlueSky Publishing, A Div. of BlueSky Medical Group Inc., 2004, 17 pages.

Landes, R.R. and I. Melnick, An Improved Suction Device for Draining Wounds, Arch. Surg., May 1972, 104, p. 707.

Landis, E.M. and J.H. Gibbon, Jr., The Effects of Alternate Suction and Pressure on Blood Flow to the Lower Extremities, Alternate Suction and Pressure, pp. 925-961.

Larichev, A.B., Vacuum Therapy of Wounds and Wound Infection, 1st. Ed., BlueSky Publishing, 2005. 237 pgs.

Lee, J.H. and H.J. Yang, Application of Medifoam B® & Negative Pressure Therapy for the Auxiliary Treatment of Pressure Sore, Dept. Plastic and Reconstructive Surg., College of Medicine, Eulji Univ., Daejeon, Korea, Abs. Sep. 31, 2004, 1 page.

Linden van der, Willem, Randomized Trial of Drainage After Cholecystectomy, Modern Operative Techniques, Voluje 141, Feb. 1981, pp. 289-294.

Lockwood, C.B., Aseptic Surgery, Drainage, Brit. Journ. Nurs., Mar. 26, 1904, p. 245.

Luchette, F.A., When Should the General Surgeon Leave the Abdomen Open, Division of Trauma, Surgical Critical Care and Burns, Loyola University Medical Center, Maywood, Illinois, 87 pages (date N/A).

Lumley, J.S.P., et al., The Physical and bacteriological Properties of Disposable and Non-Disposable Suction Drainage Units in the Laboratory, Br. J. Surg., 1974, 61, pp. 832-837.

Lundvall, J. and T. Lanne, Transmission of Externally applied Negative pressure to the Underlying Tissue: A Study on the Upper Arm of Man, Acta Physiol. Scand. 1989, 136, pp. 403-409.

Magee, C., et al., Potentiation of Wound Infection by Surgical Drains, Amer. Journ. of Surg., May 1976, 131, pp. 547-549.

Maitland and Mathieson, Suction Drainage, Brit. J. Surg Mar. 1970, 57(3), pp. 195-197.

Mayo, C.W., The One-Stage Combined Abdominoperineal Resection for Carcinoma of the Rectum, RectoSigmoid and Sigmoid, Surgical Clinics of North America, Aug. 1939, Mayo Clinic Number, pp. 1011-1012.

McFarlane, R.M., The Use of Continuous Suction under Skin Flaps, Br. Journ. Plast. Surg., pp. 77-86.

McGuire, S., Drainage after Abdominal Section, Br. Journ. of Nurs., Dec. 15,1903, pp. 447-449.

McLaughlan, James, Sterile Microenvironment for Postoperative Wound Care, The Lancet, pp. 503-504, Sep. 2, 1978.

Medela, Inc., Pleupump MK II, Aug. 14, 2001, Brochure (in German), 12 pages.

Mendez-Eastman, S., Guidelines for Using Negative Pressure Wound Therapy, Advances in Skin & Wound Care, 14(6), Nov./Dec. 2001, pp. 314-325.

Mendez-Eastman, S., When Wounds Won't Heal, RN, Jan. 1998, pp. 2-7.

Meyer and Schmieden, Bier's Hyperemic Treatment, 1908, Fig. 69-70, p. 557.

Meyer, W. and V. Schmieden, Bier's Hyperemic Treatment, Published 1908 W. B. Saunders Company. (the entire reference has been submitted, but pp. 44-65 may be the most relevant).

Miles, W.E., A Method of Performing Abdominoperineal Excision for Carcinoma of the Rectum and of the Terminal Portion of the Pelvic Colon, The Lancet, Dec. 19, 1908, pp. 1812-1813.

Miller, M.S. and C. McDaniel, Treating a Pilonidal Cystectomy Abscess Wound with the BlueSky Medical Versatile 1™ Negative Pressure Wound Therapy, The Wound Healing Center, Terre Haute, Indiana, Case Study 2004-2006, 1 page.

Miller, M.S., Negative Pressure Wound Therapy: "A Rose by Any Other Name," Ostomy/Wound Management, Mar. 2005, 51(3), pp. 44-49.

Milsom, I. and A. Gustafsson, An Evaluation of a Post-Operative Vacuum Drainage System, Curr. Med. Res. Opin. (1979), 6, pp. 160-164.

Moloney, G.E., Apposition and Drainage of Large Skin Flaps by Suction, Australian and New Zealand Journ. of Surg., pp. 173-179, 1950.

Morykwas, M.J., et al., Effects of Varying Levels of Subatmospheric Pressure on the Rate of Granulation Tissue Formation in Experimental Wounds in Swine, Abs., Ann. Plast. Surg. 2001, 47: p. 547.

Moserova, J. and E. Houskova, The Healing and Treatment of Skin Defects, 1989, pp. 116-143.

Moss, W., What is Cellulitis? Describe Some Forms of Treatment You Would Expect to be Used for Cellulitis of the Arm, Brit. Journ. Nurs., Nov. 1935, p. 282.

Mulder, G.D., Ed., et al., Clinicians' Pocket Guide to Chronic Wound Repair, Wound Healing Publications, Spartanburg, SC, 1991, pp. 54-55.

Mullner, T., et al., The Use of Negative Pressue to Promote the Healing of Tissue Defects: A Clinical Trial Using the Vacuum Sealing Technique, Br. J. Plast. Surg., Apr. 1997, 51(1), p. 79, Abs.

Musashaikhov, K.T., et al., The Course of Wound Healing under the Influence of Polyphepan in patients with Diabetes Mellitus, Abstracts, Surg. No. 5, 1997, Downloaded from internet, http://www.mediasphera.ru/surgery/97/5/e5-97ref.htm, 1 page.

Nakayama, Y., et al. "A New Method for the Dressing of Free Skin Grafts", Plastic and Reconstructive Surgery, Dec. 1990 pp. 1216-1219, UK.

Nakayama, Y., et al. "A New Method for Free Skin Grafting in Hands," Annals of Plastic Surgery, vol. 26, No. 5 May 1991, 4 pages.

Nasser, A.N., The Use of the Mini-Flap Wound Suction Drain in maxillofacial surgery, Annals of the Royal College of Surgeons of England, 1986, 68, pp. 151-153.

Navsaria, P.H., et al., Temporary Closure of Open Abdominal Wounds by the Modified Sandwich-Vacuum Pack Technique, Br. Journ. Surg., 2003, 90, pp. 718-722.

Nghiem, D.D., A Technique of Catheter insertion for Uncomplicated Peritoneal Dialysis, Surgery, Gynecology & Obstetrics, Dec. 1983, 157, pp. 575-576.

Nicholas, J.M., Options for Management of the Open Abdomen, Presentation from Emory University School of Medicine, 66 pgs.

Nightingale, K., Making Sense of wound Drainage, Nursing time Jul. 5, 1989, 85(27), pp. 40-42.

Noblett, E.A., What is an Empyema, What Operations are Undertaken for its Relief, and What Have You to Say About the After-Nursing, Brit. Journ. Nurs., Apr. 29, 1916, p. 375.

O'Byrne, C., Clinical Detection and Management of Postoperative Wound Sepsis, Nursing Clinics of North American, Dec. 1979, 14(4), pp. 727-741.

Ohotskii, V.P., et al., Usage of Vacuum Suction During the Primary Surgical Debridement of Open Limb Injuries, Sovetskaya Medicina, 1973, January, pp. 17-20 (in Russian with English translation).

Ontario Ministry of Health and Long Term Care for the Ontario Health Technology Advisory Committee, "Vacuum Assisted Closure Therapy for Wound Care, Health Technology Literature Review," Dec. 2004, Toronto, Ontario, Canada, pp. 1-57.

Orgill, D. P., et al., Microdeformational Wound Therapy—A New Era in Wound Healing, Tissue Engin. and Wound Healing Laboratory, Brigham and Women's Hospital, Business Briefing: Global Surgery—Future Direction 2005, p. 22.

Orgill, D., et al., Current Concepts and Approaches to Wound Healing, Critical Care Medicine, Sep. 1988, 16(9), pp. 899-908.

Orgill, D.P., et al., Guidelines for Treatment of Complex Chest Wounds with Negative Pressure Wound Therapy, Wounds, A Compendium of Clinical Research and Practice, Suppl. B, Dec. 2004, pp. 1-23.

Oschsner, A.J., Surgical Diagnosis and Treatment, 1921, 11, pp. 266-269.

Parker, M.J. and C. Roberts, Closed suction Surgical Wound Drainage after Orthopaedic Surgery, Cochran Database of Systematic Review 2005, 3, 3 pages.

Parulkar, B.G., et al., Dextranomer Dressing in the Treatment of Infected Wounds and Cutaneous Ulcers, J. Postgrad. Med., 1985, 31(1), pp. 28-33.

Penman, M., What Are the Signs and Symptoms of Gallstones? What Instruments Would You have Ready for the Operation? How Would You Nurse a Case After Operation?, Brit. Journ. Nurs., Aug. 9, 1919, p. 88.

Pham, C., et al., Vacuum-Assisted Closure for the Management of Wounds: An Accelerated Systematic Review, Asernip-Accelerated Review of Vacuum Assisted Wound Closure, Report No. 27, Dec. 2003, pp. 1-52.

"Pleur-evac. Adult-Pediatric, Non-Metered." Code No. A-4000. Control No. F7961J, 1 page.

Precision Medical, Power VAC+ Intermittent Aspirator, http://precisionmedical.com Downloaded from internet Apr. 10, 2006, 2 pages.

Rammensee, H.G., Untersuchung der Lymphozytenin filtrate in Implantierte PVA-Schwamme nach der Therapie infizierter Wunden mit Vakuumversiegelung, Aus dem Interfakulatären Institut für Zellbiologie der Universität Tübingen Abeilung Immunologie Abteilungsleter, 2004, 119 pgs.

Ranson, John H. M.D., Safer Intraperitoneal Sump Drainage, Surgery Gynnecology and Obstetrics, pp. 841-842, 1973 vol. 137.

Redon, H. and J. Troques, La Fermeture Sous Depression des Plaies Etendues, Academe de Chirurgie, Mar. 1954, pp. 304-306. (in French).

Redon, H., Closure of Large Wounds under a Partial Vacuum, Paris, Notes on Practical Medicine, published under L. Rouques, pp. 1-3.

Reedy, J., The Science Behind Wound Healing, UW Health Sciences/UW Medicine News and Community Relations, Winter/Spring 2005, 4 pages.

Reference Handbook of the Medical Sciences, Hyperaemia, p. 553.

Reimann, D., et al., Successful Treatment Due to Vacuum Seal Technique of a Severe Scedosporium Apiospermum Skin Infection in a Renal Transplant Recipient, Nephrol. Dial. Transplant, 2004, 19 (1), pp. 245-248.

Richter, Treatment of Inflammatory Conditions of the Skin with Hot Baths, Brit. Journ. Nurs., Aug. 25, 1906, pp. 149.

Roberts, R.H., et al., Randomised Trial of Medinorm LVS and Surgivac Drainage System after Operations for Breast Cancer May 1999, Amer. Journ. Surg., Feb. 1997, 2 pgs.

Robertson, "The Influence upon Wound Contraction of a Negative Interstitial Fluid Pressure Within Granulation Tissue," Journal of Anatomy, 1969, vol. 105, No. 1, pp. 189.

Rodrigo, J.J., et al., The Effect of Varying Degrees of Suction Pressure on Drainage of Hematomas, Dept. of Orthopaedic Surgery, University of California, David, Sacramento, California, 9 pages.

Rosser, C.J., et al., A New Technique to Manage Perineal Wounds, Infections in Urology, Mar./Apr. 2000, 4 pgs.

Royle, G.T. and B.J. Britton, Disposable Drains, Articles of the Royal College of Surgeons of England, (1984), vol. 66, 1 page.

Russ and Fleischmann, Vakuumversiegelung, List of References (in English and German), 2000, 4 pgs.

Sagi, A., Burn Hazard from Cupping—An Ancient Universal Medication Still in Practice, burns, 1988, 14(4), pp. 323-325.

Sames, C.P., Sealing of Wounds with Vacuum Drainage, Br. Med. Journ., Nov. 5, 1977, p. 1223, Correspondence.

Samson, D., et al., Wound-Healing Technologies: Low-Level Laser and Vacuum-Assisted Closure, Evidence report/Technology Assessment, No. 111, Dec. 2004, AHRQ Publication No. 05-E005-2, 97 pages.

Sandahl, L., Slides at Geisinger Medical Center, Danville, PA, Apr. 10, 1990, Correspondence, 4 pages.

Schaffer, D.B., Closed Suction Wound Drainage, Nursing97, Nov., Downloaded from internet www.springnet.com, pp. 62-64. 1997.

Schumann, D., Preoperative Measures to Promote Wound Healing, Nursing Clinics of North America, Dec. 1979, 14(4), pp. 683-699.

Scott, F., Babies in Bottles, Advance for Resp. Care Practitioners, Nov. 23, 1992, 2 pgs.

Senyutovich, R.V., Napkin Preventing Abdominal Contamination in Performance of Colonic Anastomosis, Abstracts, Downloaded from internet, http://www.rnediasphera.ru/ surgery/97/1/el-97ref.htm , 1997, 1 page.

Shaer, W.D., et al., Inexpensive Vacuum-Assisted Closure Employing a Conventional Disposable Closed-Suction Drainage System, Plastic and Reconstructive Surgery, Jan. 2001, p. 292.

Sheen, A.W., Some Experiences of Shell Wounds in the Present War, (excerpt), Brit. Journ. Nurs., Jan. 16, 1915, p. 42.

Smith, L.A., et al., Vacuum Pack Technique of Temporary Abdominal Closure: A Four-Year Experience, Amer. Surg., Dec. 1997, 63(12), pp. 1102-1108.

Specific Inflammations, Diseases of the Skin, pp. 549-550.

Stewart, M. F., et al., Cleaning v Healing, Community Outlook, Aug. 1985, pp. 22-26.

Surgidyne, Closed Systems for Management of Wound Drainage, Brochure and Catalog, Downloaded from internet, www.sterion.com, 6 pages.

Svedman, P., "A Dressing Allowing Continuous Treatment of a Biosurface," *IRCS Med. Science: Biomed. Tech.; Clinic. Med.; Surg. and Transplantation*, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Svedman, "Irrigation Treatment of Leg Ulcers," The Lancet, Sep. 3, 1983, pp. 532-534.

Swanson, L., Solving Stubborn-Wound problem Could Save Millions, Team Says, JAMC, 23 FEVR, 1999: 160(4), p. 556.

Teder, et al., "Continuous Wound Irrigation in the Pig," Journal of Investigative Surgery, 1990, vol. 3, pp. 399-407.

Tenta, L.T., et al., Suction Drainage of Wounds of the Head and Neck, Surg. Gyn. & Ob., Dec. 1989, 169, p. 558.

The Bier Treatment, Brit. Journ. Nurs., Jun. 6, 1908, p. 452.

The British Journal of Nursing, Nov. 4, 1911, p. 368.

Tittel, K. and G. Tolksdorff, Forum: VariDyne—Neue Standard in der Postoperative Wunddrainage (New Standards in Postoperative Wound Drainage), Unfallchirurgie, 1988 14(2), pp. 104-107 (in German with English Translation).

Tribble, David E. M.D., An Improved Sump Drain-Irrigation Device of Simple Construction, Archives of Surgery New York, pp. 511-513, 1972 vol. 105.

Tuberculous Joints, Nursing record & Hospital World, Apr. 28, 1894, p. 280.

Tennant, The Use of Hyperemia in the Postoperative Treatment of Lesions of the Extremeties and Thorax, Jour. A.M.A., May 8, 1915, vol. LXIV, No. 19, pp. 1548-1549.

Urschel, J.D., et al., The Effect of Mechanical Stress on Soft and Hard Tissue Repair; A Review, Br. Journ. Plast. Surg., 1988, 41, pp. 182-186.

U.S. Appl. No. 11/491,578, filed Jul. 24, 2006, Title: Negative Pressure Protection System.

U.S. Appl. No. 11/654,926, filed Jan. 17, 2007, Title: Container and Cover System.

Usypov, Y. N. and M.V. Ephfanov, Active Drainage of wounds, Dept. of Hospital Surgery, Army Medical Academy, Leningrad, Vestnik Chirurgia 1987, April Edition, pp. 42-45 (in Russian with English translation).

Valenta, A.L., Using the Vacuum Dressing Alternative for Difficult Wounds, AIN, Apr. 1994, pp. 44-45.

Van Heurn, L.W.E. and P.R.G. Brink, Prospective Randomized Trial of High versus Low Vacuum Drainage after Axillary Lymphadenectomy, Br. Journ. Surg. 1995, 82, pp. 931-932.

Van Way III, C.W., Prevention of Suction-Induced Gastric mucosal damage in Dogs, Critical Care Medicine, Aug. 1987, 15(8), pp. 774-777.

Varley, G.W. and S.A. Milner, Wound Drains in Proximal Femoral Fracture Surgery: A Randomized prospective Trial of 177 Patients, J. R. Coll. Surg. Edinb., Dec. 1995, 40, pp. 416-418.

Vijanto, J. and J. Raekallio, Local Hyperalimentation of Open Wounds, Br. J. Surg., 1976, 63, pp. 427-430.

Wackenfors, A., et al., Effects of Vacuum-Assisted Closure Therapy on Inguinal Wound Edge Microvascular Blood Flow, Wound Rep. Reg, 2004, 12, pp. 600-606.

Warren, J.C. and A.P. Gould, Ed., The International Text-Book of Surgery, 1902, 1, pp. 70-79.

Waymck, J.P., et al., An Evaluation of Aquaphor Gauze Dressing in Burned children, Abs., 2006.

Wayne, M.A., Cook Pneumothorax Catheter Set, Wayne Pneumothorax Catheter Set, Cook Critical Care, Cook Incorporated 1997, 3 pgs.

Westaby, S., Wound Care No. 11, Nursing Times, Jul. 21, 1982, pp. 41-48.

White, R.A., et al., Vacuum-Assisted Closure Complicated by Erosion and Hemorrhage of the Anterior Tibial Artery, Journal of Orthopaedic Trauma, Jan. 2005, 19(1), pp. 56-59, Abs. Cited in BlueSky internal email dtd. Nov. 9, 2005.

Williams, et al., Survey of the Use of Suction Drains in head and Neck Surgery and Analysis of Their Biomechanical Properties, J. Otolaryngol., Feb. 2003, 32(1), pp. 16-22, Abs. Downloaded from internet Nov. 30, 2003.

Windows on Medical Technology, Vacuum-Assisted Wound Closure for Chronic and Acute Wounds, , ECRI Health Technology Assessment Information Service, Oct. 2000, 38, pp. 1-21.

Witkowski, J.A. and Parish, L.C., Synthetic Dressings: Wound Healing in the '80s, Hospital Therapy, Nov. 1986, pp. 75-84.

Worth, M.H. and H.W. Andersen, The Effectiveness of Bacterial Filtration in Vented Wound Drains, Journ. of Surg. Research, 1979, 27, pp. 405-407.

Wu, P., et al., In Vitro Assessment of Water Vapour Transmission of Synthetic Wound Dressings, Biomaterials, 1995, 16(3), pp. 171-175.

Wu, W.S., et al. Vacuum therapy as an intermediate phase in wound closure: a clinical experience, Eur J Past Surg (2000) 23, pp. 174-177.

Yukhtin, V.I., et al., Surgical Treatment of Purulent Diseases of Soft tissues and Bones with the Use of Drainage-Bathing System, Content, Surg. No. 9 1997, Downloaded from internet, http://www.mediasphera.ru/surgery/97/9/e9-97ref.htm, 1 page.

Zhetimkarimov, D.S. and V.K. Ostrovsky, The Applied Significance of Anatomic Pecularities of Greater Momentum, Contents, Surg. No. 6, 1997, Downloaded from internet http://www.mediasphera.ru/surgery/97/6/e6-97ref.htm, 1 page.

Zivadinovic, Gorica, Veljko Dukic, and Sava Filipovic, Our Experience in the Treatment of Patients with Arterial Failure of the Extremities Using the Vacusac Unit, Timocki Medicinski Glasnik, Year XII, Zajecar, 1987 No. 1, pp. 55-65.

Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajecar, 1986, No. 3-4, pp. 161-164.

Chariker, M.E., et al, "Effective Management of Incisional and Cutaneous Fistulae with Closed Suction Wound Drainage," Contemporary Surgery. Jun. 1989, pp. 59-63, vol. 34 USA.

Biblehimer, Helen L., "Dealing With a Wound that Drains 1.5 Liters a Day," RN, Aug. 1986, pp. 21-23, USA.

Wooding-Scott, Margaret, et.al, "No Wound is Too Big for Resourceful Nurses," RN, Dec. 1988, pp. 22-25, USA.

Garcia-Renaldi, Raul, et al, "Improving the Eficiency of Wound Drainage Catheters," Journal of Surgery (?), Sep. 1975, pp. 372-373, vol. 130.

Schwab, Peter M. and Kelly, Keith A., "Primary closure of the Perineal Wound After Proctectomy,"Mayo Clinic Proc., Mar. 1974, pp. 176-179, vol. 49, USA.

Ramirez, Oscar M., et al, "Optimal Wound Healing Under Op-Site Dressing," pp. 474-475, vol. 73, No. 3.

Raffl, Arthur B., "Use of Negative Pressure Under Skin Flaps After Radical Mastectomy,"Dept. of Surgery, State Univ. of N.Y., College of Medicine, Syracuse, NY, Submitted for publication Apr. 1953, p. 1048, USA.

Knight, Marie Ray, A Second Skin for Patients with Large Draining Wounds, Nursing, Jan. 1976, p. 37, USA.

Finley, John M.,"Practical Wound Management," pp. 45, 127, 143, 149, 207.

Spengler, Michael D., el al, "Performance of Filtered Sump Wound Drainage Tubes", Surgery, Gynecology & Obstetrics, Mar. 1982, pp. 333-336, vol. 54, USA.

Kohlman, Phyllis A., et al, "Pouching Procedure to Collect Drainage From Around a Biliary Drainage Catheter," Ostomy/Wound Management, Nov./Dec. 1991, pp. 47-50, vol. 37.

Alper, Joseph, C., "Recent Advances in Moist Wound Healing," Southern Medical Journal, Nov. 1988, pp. 1398-1404, vol. 79, No. 11 USA.

Reid, Daniel P., "Information on Cupping or using suction Cups on Wounds and for healing purposes", From Chinese Herbal Medicine.

Taylor, Virginia, Meeting the Challenge of Fistulas & Draining Wounds, Nursing, Jun. 1980, pp. 45-51, USA.

"General Characteristics of Wound Healing and Russian Classification of Wound Healing Process."

Davydov, Yu. A., et al, Article in Russian (?): Abstract in English: "Vacuum Therapy in the Treatment of Purulent Lactation Mastitis", pp. 66-70.

Davydov, Yu. A., et al, Article in Russian (?): Abstract in English: "The Bacteriological and Cytological Assessment of Vacuum Therapy of Purulent Wounds", pp. 48-52.

Article 3, Article in Russian (?), 1991, pp. 126-128.

Article 4, Article in Russian (?), 1991, pp. 132-135.

Alexander, J. Wesley, "Prevention of Wound Infections," The American Journal of Surgery, Jul. 1976, pp. 59-63, vol. 132, USA.

Sheppard, M.D., "Sealed Drainage of Wounds", The Lancet, Jun. 14, 1952, pp. 1174-1176.

Putney F. Johnson, "The Use of Continuous Negative Pressure after Laryngectomy and Radical Neck Dissection", Surgery, Gynecology & Obstetrics, Aug. 1956, pp. 244-246, USA.

Brummelkamp, W.H., et al, "High-vacuum drainage and primary perineal wound closure in abdominoperineal excision of the rectum", The Netherlands Journal of Surgery, 1991 pp. 236-238, Netherlands.

Miles, W. Ernest, "Technique of the Radical Operation for Cancer of the Rectum", The British Journal of Surgery, pp. 292-304, United Kingdom.

Unknown, "Wound Suction", Nursing, Oct. 1975, pp. 52-53, USA.

Brubacher, Lynda L., "To Heal A Draining Wound", RN, Mar. 1982, pp. 30-35, USA.

Betancourt, Sergio, "A Method of Collecting the Effluent from Complicated Fistual of the Small Intestine," Dept. of Surgery, Allegheny General Hospital, Pittsburgh, p. 375, USA.

Wolthuis, Roger A., et al, "Physiological Effects of Locally Applied Reduced Pressure in Man," Physiological Reviews, Jul. 1974, pp. 566-595 vol. 54, No. 3, USA.

Zamierowski, David S., Letter:"All Foam Sponges are not Equal in Vacuum Dressings," British Journal of Plastic Surgery, 1999, 52, 78-81, p. 79, United Kingdom.

Spahn, Slide presented at the WOCN meeting in Ontario, California, Sep. 2001.

Unknown, "The RN Magazine/University of California Continuing Education Curriculum; Examination on 'To heal a draining wound'", RN, Mar. 1982, p. 36, USA.

Unknown, Medela product information in, English Summary: "Pieupump MK II is the new micro-data controlled thoracic drainage".

U.S. Appl. No. 12/186,424, filed Aug. 5, 2008, Krohn.

Author Unknown, Hyperemia by Suction Apparatus, Chapter VIII, 74-85.

Froberg, Birgitta et al., Vacusac Therapy—A Supplement to the Treatment of Varicose Ulcers? (Stockholm) 1990.

Harle, A.Z. Orthop., Schwachstellen herkommlicher Drainagen, 1989, 127: 513-517.

U.S. Appl. No. 12/186,424, filed Aug. 5, 2008, and its ongoing prosecution history, including without limitation Office Actions, Amendments, Remarks, and any other potentially relevant documents, Kenneth P. Krohn.

Hargens et al., *Space Physiology Laboratory, Life Science Division, NASA Ames Research Center, "Control of Circulatory Functions in Altered Gravitational Fields."* Physiologist, Feb. 1992;35(1 Suppl):S80-3. Control of circulatory function in altered gravitational fields.

Landis, E.M. and J.H. Gibbon, Jr., *The Effects of Alternate Suction and Pressure on Blood Flow to the Lower Extremities, Alternate Suction and Pressure*, J Clin Invest. Sep. 1933, 12(5): 925-961.

Meyer, W. & Schmieden, V., *Bier's Hyperemic Treatment, W B. Saunders Company* 1908, (the entire reference has been submitted, but pp. 44-65 may be the most relevant).

U.S. Appl. No. 12/375,191, filed Jan. 26, 2009, and its ongoing prosecution history, including without limitation Office Actions, Amendments, Remarks, and any other potentially relevant documents, Richard S. Weston, et al.

Nursing75, Wound Suction: Better Drainage with Fewer Problems: Oct. 1975—vol. 5—Issue 10—p. 52-55.

Thomas, Stephen "Wound Management and Dressings" 35-42 (1990).

* cited by examiner

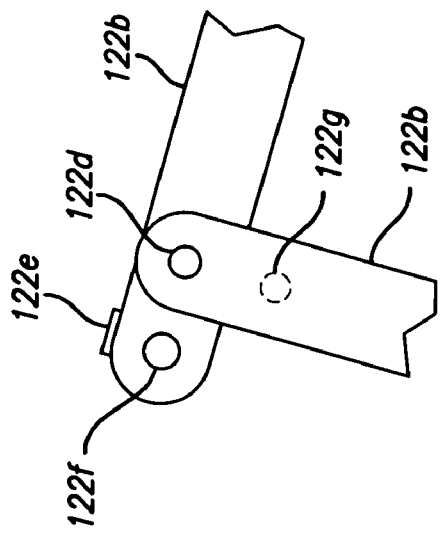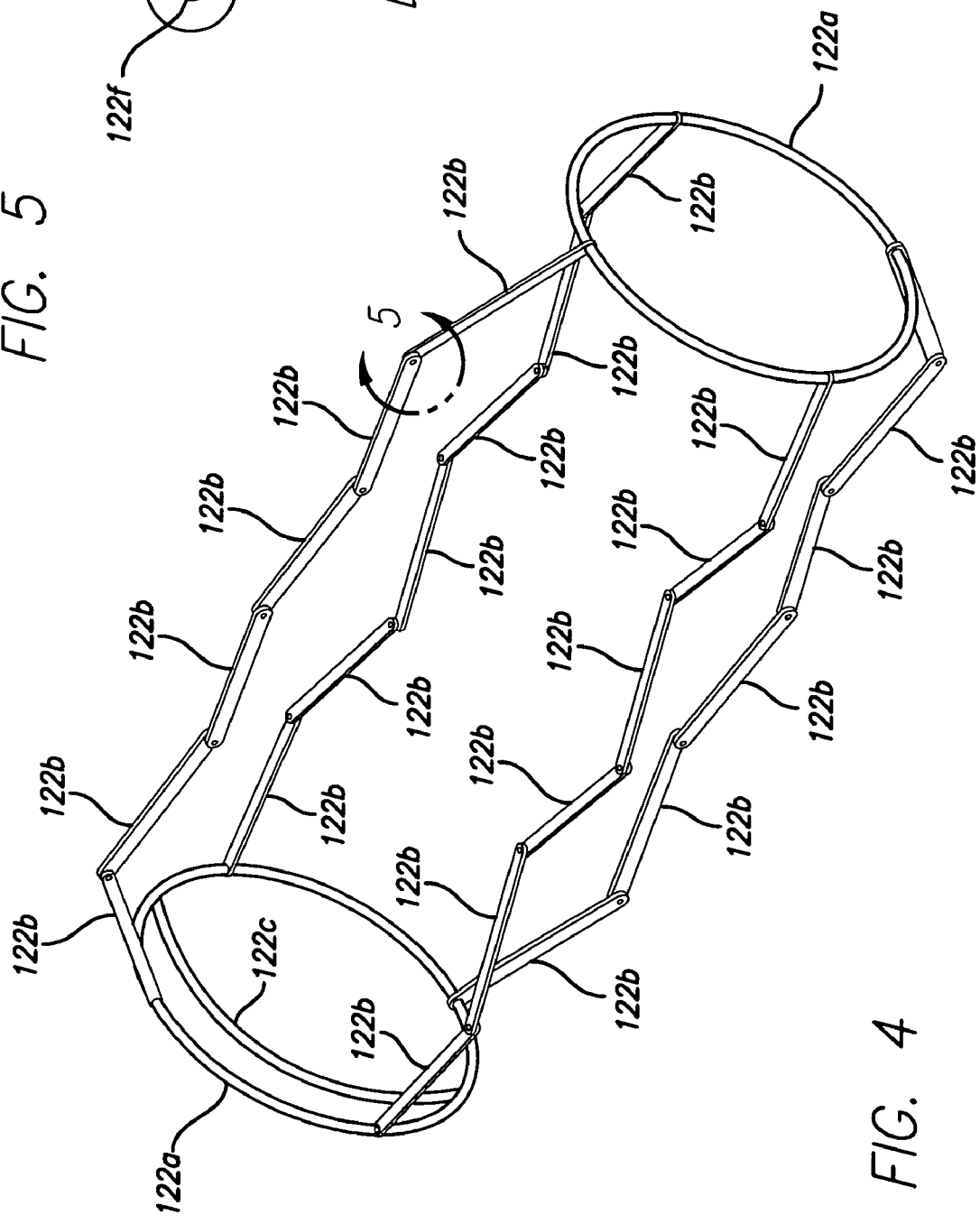
FIG. 5
FIG. 4

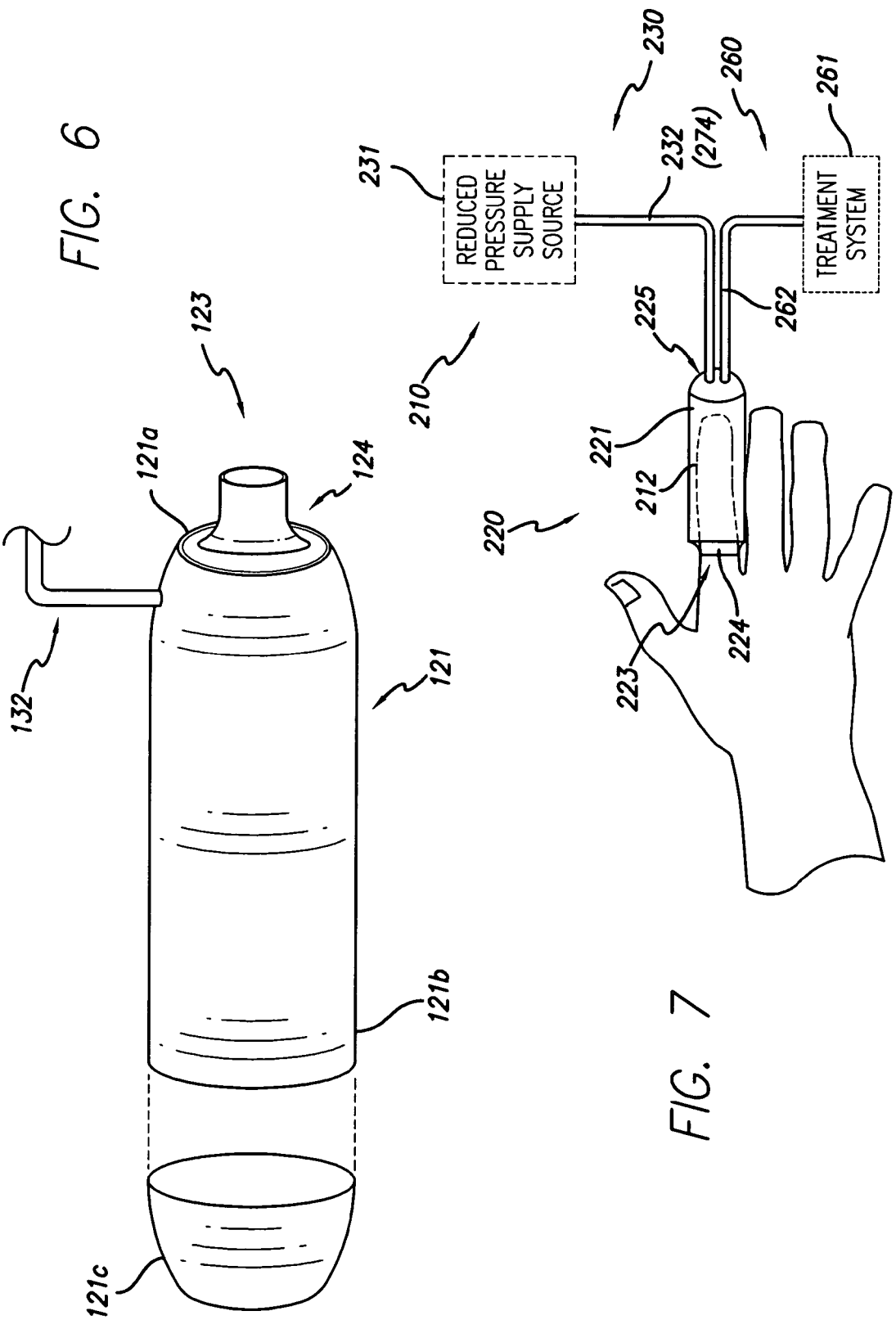

HYPOBARIC CHAMBER TREATMENT SYSTEM

CROSS REFERENCES TO OTHER APPLICATIONS

This application claims the benefit of U.S. provisional application No. 60/573,653, filed on May 21, 2004. The full disclosure of this provisional application is incorporated herein by reference.

BACKGROUND

The present invention generally relates to administration of reduced pressure to objects or portions of objects that require the application of reduced pressure as a part of treatment of such objects or portions of objects. For example, in some embodiments, the present invention comprises an improved apparatus and method for treating wounds and other infirmities and conditions on a portion of a patient's body by applying reduced pressure to the portion of the body for which treatment is desired. In this context, the terms "wound," "infirmity," "condition" and "body" are to be interpreted broadly, to include any body part of a patient that may be treated using reduced pressure. As another example, in other embodiments, the present invention comprises an improved apparatus and method for reduced pressure treatment related to industrial-type processes, such as degassing materials and insect control.

The treatment of open or chronic wounds that are too large to spontaneously close or otherwise fail to heal by means of applying reduced pressure to the site of the wound is well known in the art. Examples of such treatment systems are disclosed in U.S. patent application Ser. No. 10/652,100 (filed on Aug. 28, 2003), Ser. No. 11/026,733 (filed on Dec. 30, 2004), Ser. No. 11/064,813 (filed on Feb. 24, 2005), Ser. No. 11/095,859 (filed by the present inventor with others on Mar. 31, 2005) Ser. No. 11/098,265 (filed on Apr. 4, 2005), and Ser. No. 11/098,203 (filed on Apr. 4, 2005), which were filed by the present inventor with the U.S. Patent and Trademark Office. The disclosures of these U.S. patent applications are incorporated herein by reference.

Reduced pressure wound treatment systems currently known in the art commonly involve placing a cover that is impermeable to liquids over the wound, using various means to seal the cover to the tissue of the patient surrounding the wound, and connecting a source of reduced pressure (such as a vacuum pump) to the cover in a manner so that an area of reduced pressure is created under the cover in the area of the wound. There are, however, certain instances where it is advantageous to have a wound treatment system that covers the entire portion of the body of the patient in the area of the wound, rather than merely the surface of the body immediately surrounding the wound. For example, certain types of burns that are treatable by reduced pressure may require treating a relatively large area of the patient's body with reduced pressure. In these cases, a device that covers the entire portion of the body to be treated would be advantageous. In addition, it is possible to treat and alleviate certain other infirmities using reduced pressure. Such infirmities may include lymphedema, venous insufficiency and stasis, and varicose veins. In the case of lymphedema, the patient suffers from an abnormal interstitial accumulation of tissue fluid. The mechanism for this accumulation is impairment of normal fluid uptake by the lymphatic vessels or excessive production of tissue fluid, which is caused by venous obstruction that increases capillary blood pressure. Common causes of lymphedema include neoplastic obstruction of lymphatic flow, postoperative interference with lymphatic flow, infectious blockade of lymphatics, and radiation damage to lymphatics. In the case of venous insufficiency and stasis, blood circulation through the venous system is inadequate. This condition may be caused by congestion or by failure of the valves that regulate the flow of blood in the veins to operate normally. In the case of varicose veins, the veins become enlarged and dilated, which may lead to venous insufficiency and stasis. It is well known in the art that application of pressure to the portions of the body of the patient affected by these infirmities may provide relief from some of the symptoms of the infirmities. A device that is capable of enclosing and providing reduced pressure treatment to an entire portion of a patient's body affected by such infirmities would be advantageous because it would be capable of providing this required application of pressure.

There are devices extant in the art that may provide this reduced pressure treatment to the entire portion of a patient's body. An example of this type of device is disclosed in U.S. patent application Ser. No. 11/075,020, entitled "Enclosure-Based Reduced Pressure Treatment System," which was filed by the present inventor (among others) with the U.S. Patent and Trademark Office on Mar. 8, 2005. The disclosure of this U.S. patent application is also incorporated herein by reference. Such devices, however, are positioned immediately adjacent to the tissue of the patient. In some cases, this may cause irritation of the skin or other tissue of the patient. In other cases, this may cause pain or discomfort for the patient. Other devices may provide reduced pressure treatment to the entire portion of a patient's body without contacting tissue in the area of the patient to be treated, but the devices may be heavy due to the nature of their construction. In addition, such devices may be large and unwieldy, so that they occupy a substantial amount of space when not in use. This may result in the devices taking up excessive amounts of storage space. In both cases, these characteristics may also prevent the devices from being portable. In yet other cases, the devices may be used in circumstances where it is not necessary to avoid contact with patient tissue, but the devices may become contaminated by exudate aspirated from the wound while in use.

Therefore, there is a need for a reduced pressure treatment system capable of enclosing the entire portion of a patient's body to be treated for a wound or other infirmity in a manner so that the system does not contact certain portions of the body of the patient. This includes the case of distal extremities, such as fingers and toes. There is also a need for such system to evenly distribute pressure on the surface of the portion of the body to be treated in certain instances. There is also a need for a reduced pressure treatment system that is lightweight. In addition, there is a need for a reduced pressure treatment system that is collapsible, so that it may be collapsed when not in use, requiring less storage space. Further, there is a need for a reduced pressure treatment system enclosing a portion of the body that provides for efficient removal of any fluid aspirated from the portion of the body being treated. There is also a need for a reduced pressure treatment system that is relatively inexpensive, while meeting the needs described above. Finally, there is a need for a reduced pressure treatment system that meets all or some of the needs described above, but where the system may be used in reduced pressure applications other than medical treatment.

SUMMARY

The present invention is directed to a reduced pressure treatment appliance and methods that satisfy the needs described above. As described in greater detail below, they have many advantages over existing reduced pressure treatment apparatus and methods when used for their intended purpose, as well as novel features that result in a new reduced pressure treatment appliance and methods that are not anticipated, rendered obvious, suggested, or even implied by any of the prior art apparatus or methods, either alone or in any combination thereof.

In accordance with the present invention, an appliance is provided for treating a portion of a body by applying reduced pressure (i.e., pressure that is below ambient atmospheric pressure) to the portion of the body to be treated in a controlled manner for a selected time period in a manner that overcomes the disadvantages of currently existing apparatus. For example, the application of reduced pressure to a wound provides such benefits as faster healing, increased formation of granulation tissue, closure of chronic open wounds, reduction of bacterial density within wounds, inhibition of burn penetration, and enhancement of flap and graft attachment. Wounds that have exhibited positive response to treatment by the application of negative pressure include infected open wounds, decubitus ulcers, dehisced incisions, partial thickness burns, and various lesions to which flaps or grafts have been attached. In addition, applying reduced pressure to portions of the body affected by lymphedema, venous insufficiency and stasis, varicose veins, and other conditions provides benefits such as increasing the circulation of lymph through the lymphatic system, increasing the circulation of blood through the venous system, faster healing of such conditions, and relief from the symptoms of such conditions. Further, the appliance may also be used in other types of applications requiring the administration of reduced pressure to an object or a portion of an object.

In a first version of the present invention, an appliance for administering reduced pressure treatment to an object or a portion of an object is comprised of a flexible chamber having an opening, a collapsible frame, sealing means (which are described in more detail below) to seal the opening, and reduced pressure supply means (which are also described in more detail below). The flexible chamber is generally sized to enclose the object or the portion of the object to be treated and adapted to maintain reduced pressure within the volume of the flexible chamber. The collapsible frame supports the flexible chamber away from the object or the portion of the object to be treated while the appliance is in use. The sealing means (which are described in more detail below) seal the opening so that reduced pressure may be maintained within the volume of the flexible chamber. The reduced pressure supply means operably connect the flexible chamber to a reduced pressure supply source that provides a supply of reduced pressure to the flexible chamber, so that the volume within the flexible chamber is supplied with reduced pressure by the reduced pressure supply source.

In this first version of the present invention, the flexible chamber and the collapsible frame may be collapsed to a smaller size when the appliance is not in use. In some embodiments of this first version of the invention, the collapsible frame is further comprised of at least one inflatable member, wherein the at least one inflatable member is inflated with a pressurized fluid when the appliance is in use and may be deflated when the appliance is not in use. In these embodiments, the appliance is further comprised of a pressurized fluid supply source and pressurized fluid supply means to operably connect the collapsible frame to the pressurized fluid supply source, so that the at least one inflatable member is supplied with the pressurized fluid by the pressurized-fluid supply source. In some embodiments, the collapsible frame is comprised of at least two inflatable members and the at least two inflatable members are operably connected together so that the pressurized fluid may flow between them. In other embodiments, the collapsible frame is comprised of a plurality of rigid or semi-rigid frame members and frame member connecting means to connect the plurality of rigid or semi-rigid frame members together, so that the plurality of rigid or semi-rigid frame members may be collapsed when the appliance is not in use. In yet other embodiments, the flexible chamber is comprised of a flexible or semi-flexible polymer material.

In some embodiments of this first version of the present invention, the appliance administers reduced pressure treatment to a portion of a body and is comprised of a treatment device, a pressurized fluid system, and a vacuum system. In these embodiments, the treatment device is further comprised of a flexible chamber having an opening, a collapsible frame, and sealing means (described in more detail below) to seal the opening so that reduced pressure may be maintained within the volume of the flexible chamber. The flexible chamber is generally sized to enclose the portion of the body to be treated and adapted to maintain reduced pressure within the volume of the flexible chamber. The collapsible frame is comprised of at least one inflatable member, wherein the at least one inflatable member is inflated with a pressurized fluid when the appliance is in use and may be deflated when the appliance is not in use. In these embodiments, the collapsible frame supports the flexible chamber away from the portion of the body to be treated while the appliance is in use and the flexible chamber and the collapsible frame may be collapsed to a smaller size when the appliance is not in use. The pressurized fluid system is comprised of a pressurized fluid supply source and pressurized fluid supply means to operably connect the collapsible frame to the pressurized fluid supply source, so that the at least one inflatable member of the collapsible frame is supplied with pressurized fluid by the pressurized fluid supply source. The vacuum system is comprised of a reduced pressure supply source and reduced pressure supply means to operably connect the flexible chamber to the reduced pressure supply source, so that the reduced pressure supply source provides a supply of reduced pressure to the volume within the flexible chamber. In some embodiments, the pressurized fluid is compressed air and the pressurized fluid supply source is an air compressor. In other embodiments, the sealing means is comprised of a flexible sleeve. In yet other embodiments, the reduced pressure supply source may be comprised of a vacuum pump and the reduced pressure supply means may be comprised of flexible tubing. In yet other embodiments, the vacuum source may be further comprised of a suction bulb system, which is described in more detail below. In some embodiments, the reduced pressure within the volume of the flexible chamber in the area of the portion of the body to be treated is in the range from approximately 20 mm of Hg below atmospheric pressure to approximately 125 mm of Hg below atmospheric pressure. In other embodiments, the reduced pressure may be applied in a cyclic nature, the cyclic nature providing alternating time periods of application of reduced pressure and without application of reduced pressure. In still other embodiments, the treatment device further comprises a treatment port operably attached to the flexible chamber. The treatment port permits fluids and other instrumentalities to be introduced into the volume within the flexible chamber. In further embodiments, the treatment device further comprises a forced entry treatment system operably connected to the flexible chamber for introducing ancillary fluids into the volume within the flexible chamber.

In other embodiments of this first version of the invention, the appliance administers reduced pressure treatment to a portion of a body and is comprised of a treatment device, which is also comprised of flexible chamber and collapsible frame substantially the same as described above. The appliance also comprises a vacuum system, which is substantially the same as described above, and a drainage system, which is described in more detail below. The drainage system is operably disposed between the flexible chamber and the portion of the body to be treated. In some of these embodiments, the drainage system further comprises an overlay, which is sized to be placed over and enclose a part of the portion of the body to be treated, and overlay sealing means to operably seal the overlay to the body. In some of these embodiments, the overlay is comprised of a semi-permeable material, so that reduced pressure may be maintained in the volume under the overlay at said part of the body. In other embodiments, the drainage system further comprises draining means extending from the volume under the overlay at said part of the body to an area outside the volume of the flexible chamber so that exudate aspirated from said part of the body may be drained from said part of the body to such outside area. In some of these embodiments, the area outside the volume of the flexible chamber is the reduced pressure supply source, so that the draining means is in fluid communication with the reduced pressure supply source and reduced pressure is supplied by the draining means to the volume under the overlay at said part of the body. In other embodiments, the draining means is further comprised of a collection system that is operably positioned between the overlay and the reduced pressure supply source. The collection system comprises a container to receive and hold fluid aspirated from said part of the body. The collection system may also further comprise pressure halting means to halt the application of reduced pressure to the volume under the overlay at said part of the body when the fluid in the container exceeds a predetermined amount. The drainage system may also further comprise wound packing means disposed between the overlay and said part of the body.

In other embodiments of this first version of the present invention, the appliance administers reduced pressure treatment to a portion of a body and is comprised of a treatment device and a vacuum system. In these embodiments, the treatment device is further comprised of a flexible chamber having an opening, a collapsible frame, and sealing means (described in more detail below) to seal the opening so that reduced pressure may be maintained within the volume of the flexible chamber. The flexible chamber is generally sized to enclose the portion of the body to be treated and adapted to maintain reduced pressure within the volume of the flexible chamber. The collapsible frame, however, is comprised of a plurality of rigid or semi-rigid frame members and frame member connecting means to connect the plurality of rigid or semi-rigid frame members together. The collapsible frame supports the flexible chamber away from the portion of the body to be treated while the appliance is in use and the flexible chamber and the collapsible frame may be collapsed to a smaller size when the appliance is not in use. The vacuum system and other features, characteristics and operation of this appliance is substantially the same as described above.

The present invention also includes a method of administering reduced pressure treatment to an object or a portion of an object using the embodiments of the first version of the invention described above. Generally, the method comprises the steps of: (1) providing an appliance for administering reduced pressure to the object or portion of the object, as described above; (2) positioning the appliance for use, so that the flexible chamber and collapsible frame are in an extended state; (3) positioning the object or portion of the object to be treated relative to the appliance so that the object or portion of the object to be treated is positioned within the volume of the flexible chamber; (4) sealing the opening of the flexible chamber using the sealing means, so that reduced pressure may be maintained in the volume within the flexible chamber; (5) operably connecting the flexible chamber with the reduced pressure supply source using the reduced pressure supply means so that reduced pressure is supplied to the volume within the flexible chamber; and (6) maintaining the reduced pressure in the volume within the flexible chamber until the object or portion of the object being treated has progressed toward a selected stage of treatment. In other embodiments, the method further comprises the steps of removing the object or portion of the object to be treated from the appliance after the selected stage of treatment has been reached and collapsing the appliance. Where the collapsible frame is further comprised of at least one inflatable member, the step of positioning the appliance for use, so that the flexible chamber and collapsible frame are in an extended state, is further comprised of inflating the at least one inflatable member with the pressurized fluid using the pressurized fluid supply source and pressurized fluid supply means. Where the collapsible frame is further comprised of a plurality of rigid or semi-rigid frame members and frame member connecting means to connect the plurality of rigid or semi-rigid frame members together, the step of positioning the appliance for use, so that the flexible chamber and collapsible frame are in an extended state, is further comprised of the step of extending the plurality of rigid or semi-rigid frame members.

In a second version of the present invention, an appliance for administering reduced pressure treatment to a distal extremital portion of a body, such as a finger or toe, is comprised of a rigid or semi-rigid chamber having an opening, sealing means (described in more detail below) to seal the opening so that reduced pressure may be maintained within the volume of the rigid or semi-rigid chamber, and reduced pressure supply means. The rigid or semi-rigid chamber is generally sized to enclose the distal extremital portion of the body and adapted to maintain reduced pressure within the volume of the rigid or semi-rigid chamber. The reduced pressure supply means operably connects the rigid or semi-rigid chamber to a reduced pressure supply source that provides a supply of reduced pressure to the rigid or semi-rigid chamber, so that the volume within the rigid or semi-rigid chamber is supplied with reduced pressure by the reduced pressure supply source. In some of these embodiments, the sealing means may be comprised of a flexible sleeve. In other embodiments, the appliance may further comprise an ancillary treatment system operably attached to the rigid or semi-rigid chamber. The ancillary treatment system permits fluids and other instrumentalities and treatment means to be introduced into the volume within the rigid or semi-rigid chamber. The appliance may also be further comprised of the reduced pressure supply source, which may be comprised of a vacuum pump or a suction bulb system, which is described in more detail below.

In a third version of the present invention, the appliance administers reduced pressure treatment to a portion of a body and comprises a chamber, a semi-permeable liner, sealing means (which are described in more detail below), and reduced pressure supply means (which are also described in more detail below). The chamber has an opening, is sized to enclose the portion of the body to be treated, is adapted to maintain reduced pressure within the volume thereof, and is supported away from the portion of the body to be treated when the appliance is in use. The semi-permeable liner is disposed between the chamber and the portion of the body positioned within the chamber. The sealing means is used to seal the opening and to seal the semi-permeable liner to the body, so that reduced pressure may be maintained within the volume of the chamber and the volume of the semi-permeable liner. The reduced pressure supply means operably connects the chamber to a reduced pressure supply source that provides a supply of reduced pressure to the chamber, so that the volume within the chamber is supplied with reduced pressure by the reduced pressure supply source. In some embodiments, the chamber is comprised of a rigid or semi-rigid material. In other embodiments, the chamber is comprised of a flexible chamber and a collapsible frame, as described above. In other embodiments, the appliance further comprises a drainage system operably disposed between the semi-permeable liner and the portion of the body to be treated. In yet other embodiments, the sealing means are comprised of a flexible sleeve that extends from the portion of the chamber approximately adjacent to the opening to a portion of the semi-permeable liner.

In other embodiments of this third version of the present invention, the appliance is comprised of a treatment device and a vacuum system. The treatment device is further comprised of a chamber having an opening, sealing means (described in more detail below) to seal the opening so that reduced pressure may be maintained within the volume of the chamber, a semi-permeable liner, and liner sealing means (also described in more detail below). The chamber is generally sized to enclose the portion of the body to be treated and is supported away from the portion of the body to be treated when the appliance is in use. The semi-permeable liner is operably disposed between the chamber and the portion of the body positioned within the chamber. The liner sealing means is used to seal the semi-permeable liner to the chamber and around a portion of the body so that reduced pressure may be maintained in the volume within the chamber and the volume within the semi-permeable liner. The vacuum system has substantially the same structure, features, characteristics and operation as the embodiments of the vacuum systems described above. In other embodiments, the treatment device may also comprise a treatment port operably attached to the chamber or a forced entry treatment system operably connected to the chamber.

In its various versions and embodiments, the present invention therefore meets the needs discussed above in the Background section. For example, the appliance of the present invention represents a reduced pressure treatment system capable of enclosing the entire portion of a patient's body to be treated for a wound or other infirmity in a manner so that the system does not contact certain portions of the body of the patient. This is also true in the case of distal extremities, such as fingers and toes. The appliance also provides for evenly distributed pressure on the surface of the portion of the body to be treated in certain instances. The appliance may also be constructed of lightweight materials. In some embodiments, the appliance is also collapsible, so that it may be collapsed when not in use, requiring less storage space. The appliance also has features that separately enclose a portion of the body, providing for efficient removal of any fluid aspirated from the portion of the body being treated. The appliance should also be relatively inexpensive to produce, while meeting the needs described above. Finally, in various embodiments, the appliance meets all or some of the needs described above and may be used in reduced pressure applications other than medical treatment.

There has thus been outlined, rather broadly, the more primary features of the present invention. There are additional features that are also included in the various embodiments of the invention that are described hereinafter and that form the subject matter of the claims appended hereto. In this respect, it is to be understood that the invention is not limited in its application to the details of construction and to the arrangements of the components set forth in the following description or illustrated in the following drawings. This invention may be embodied in the form illustrated in the accompanying drawings, but the drawings are illustrative only and changes may be made in the specific construction illustrated and described within the scope of the appended claims. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

The foregoing summary, as well as the following detailed description of the preferred embodiments of the present invention, will be better understood when read in conjunction with the appended drawings, in which:

FIG. 4 is a perspective view of the collapsible frame portion of the embodiment of the treatment device illustrated in FIG. 2, without the flexible chamber covering the collapsible frame portion;

FIG. 5 is an enlarged elevation view of a joint comprising the embodiment of the collapsible frame portion illustrated in FIG. 4;

FIG. 6 is a perspective view of the flexible chamber portion of the embodiment of the treatment device illustrated in FIG. 3, without the collapsible frame portion;

FIG. 7 is a view of an embodiment of an appliance comprising the present invention, in which an embodiment of a treatment device, shown in perspective view, encloses a portion of the finger of a patient, and in which embodiments of a vacuum system and an ancillary treatment system, depicted generally and shown partially in schematic elevation view, provide reduced pressure and various treatment means, respectively, to the treatment device;

DETAILED DESCRIPTION OF THE PREFERRED EMBODIMENTS

In accordance with the present invention, an appliance and methods for using the appliance are provided for administering reduced pressure to all or a portion of an object. The description of the present invention set forth herein is directed primarily toward use of the appliance and methods for treatment of wounds and other infirmities and conditions on a portion of a patient's body. In these cases, an appliance is provided for treating a portion of the body of a patient by applying reduced pressure (i.e., pressure that is below ambient atmospheric pressure) to the portion of the body to be treated in a controlled manner for a selected time period in a manner that overcomes the disadvantages of currently existing apparatus. It is to be noted, however, that the appliance and methods may be used to provide reduced pressure treatment for other objects and purposes. For example, in some embodiments, the present invention may be used for reduced pressure treatment related to industrial-type processes, such as degassing materials and insect control. Such uses are encompassed within the scope of the present invention to the extent they are included within the scope of the appended claims.

Figure 1:
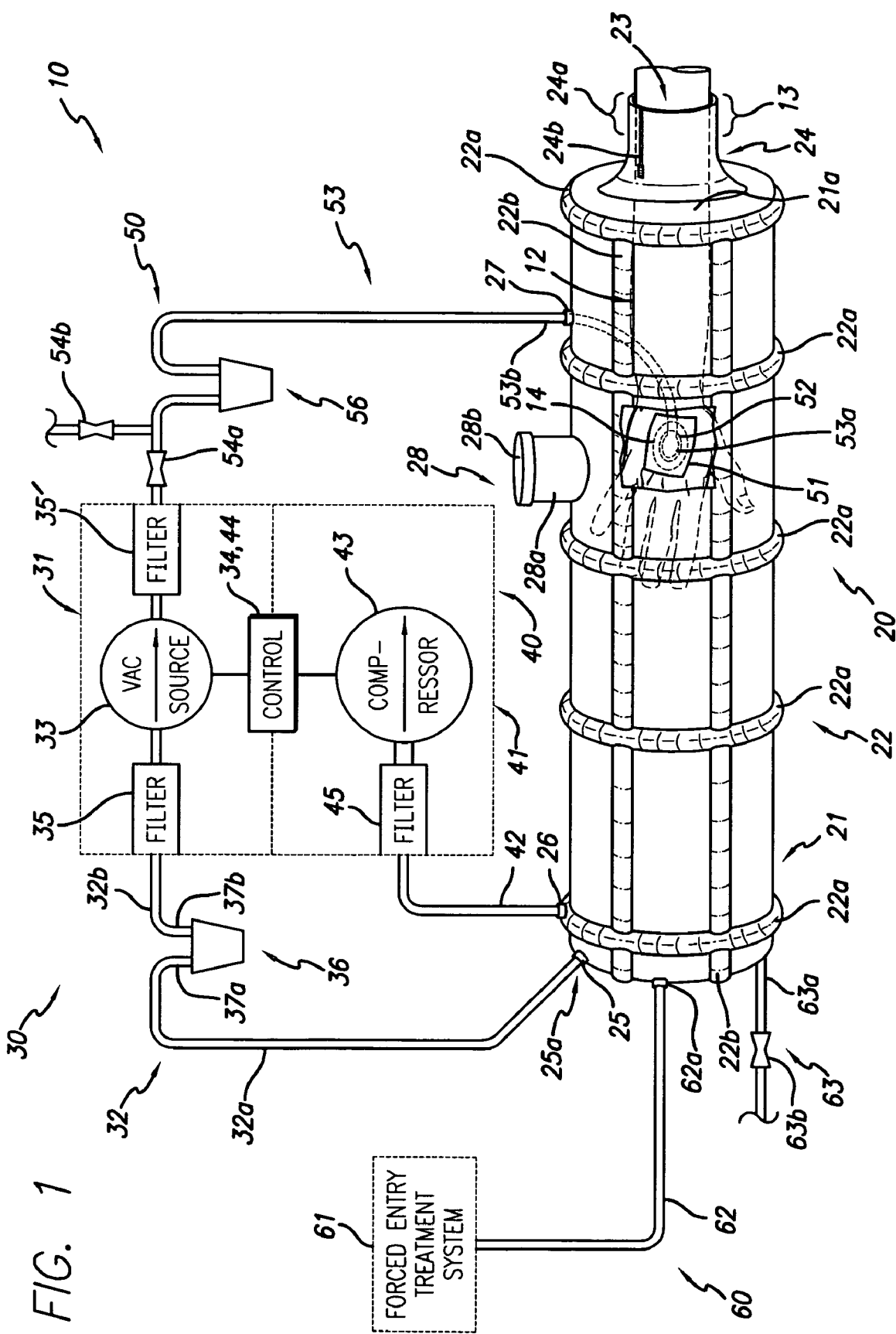
FIG. 1 is a view of an embodiment of an appliance comprising the present invention, in which an embodiment of a treatment device, shown in partially broken-away perspective view, encloses the lower arm portion of a patient, and in which embodiments of a vacuum system, a pressurized fluid system, and a forced entry treatment system, depicted generally and shown partially in schematic elevation view, provide reduced pressure, pressurized fluid, and various treatment means, respectively, to the treatment device.

An embodiment of an appliance 10 of a first version of the invention is illustrated in FIG. 1. In this embodiment, the appliance 10 is generally comprised of a treatment device 20, a vacuum system (illustrated schematically in part and generally designated 30), a pressurized fluid system (illustrated schematically in part and generally designated 40), a drainage system 50, and a forced entry treatment system (illustrated schematically in part and generally designated 60). The treatment device 20 is generally comprised of a flexible chamber 21 and a collapsible frame 22, which is generally comprised of a plurality of inflatable members 22a, 22b that are interconnected in a manner so that fluid may flow between them. The flexible chamber 21 has an opening 23 at one end, which is sealed using sealing means that are described in more detail below. In the illustrated embodiment, the lower arm portion 12 of a patient extends through the opening 23 so that the lower arm portion 12 may be treated with reduced pressure by the appliance 10. The vacuum system 30, which is described in more detail below, is generally comprised of a reduced pressure supply source, generally designated 31, and reduced pressure supply means 32 that operably connect the reduced pressure supply source 31 to the flexible chamber 21 so that reduced pressure is supplied to the volume within the flexible chamber 21 at the portion of the body 12 to be treated, as described in more detail below. The reduced pressure supply source may also provide a supply of reduced pressure to the drainage system 50, as described in more detail below. The pressurized fluid system 40, which is described in more detail below, is generally comprised of a pressurized fluid supply source, generally designated 41, and pressurized fluid supply means 42 that operably connect the pressurized fluid supply source 41 to the collapsible frame 22 so that pressurized fluid is supplied to the inflatable members 22a, 22b comprising the collapsible frame 22, as described in more detail below. The forced entry treatment system 60 is used to provide various treatments to the portion of the body 12 within the volume of the flexible chamber 21, as described in more detail below. The drainage system 50 may generally be used to remove exudate aspirated from the portion of the body 12 to be treated, as described in more detail below.

In the embodiment of the appliance 10 illustrated in FIG. 1, the treatment device 20 is comprised of the flexible chamber 21 and the collapsible frame 22. The flexible chamber 21 may be of almost any size, and is generally sized to enclose the object or the portion of the object (the lower arm portion 12 in FIG. 1) to be treated. In addition, the flexible chamber 21 may be of almost any shape. Thus, even though the flexible chamber 21 of the appliance 10 of FIG. 1 is generally cylindrical, the flexible chamber 21 may be of other shapes in other embodiments of the present invention. For example, the flexible chamber 21 may also be cubical, spherical, spheroidal, hexahedral, polyhedral, or have arcuate or linear shaped portions, or may be comprised of any combination of any such shapes, in other embodiments. The preferred size and shape of the flexible chamber 21 is thus dependent upon the size and shape of the object or portion of the object to be treated, the magnitude of reduced pressure to be maintained within the volume of the flexible chamber 21, the nature of the reduced pressure treatment desired, and the preference of the user of the appliance 10. The flexible chamber 21 is also adapted to maintain reduced pressure within its interior volume. Thus, the flexible chamber 21 may be constructed of almost any flexible or semi-flexible, opaque or transparent, fluid-impermeable material that is currently known in the art or that may be developed in the art in the future, as long as the flexible chamber 21 is able to generally maintain its shape while reduced pressure is present in the interior volume of the flexible chamber 21 and the flexible chamber 21 is supported by the collapsible frame 22. For example, the flexible chamber 21 may be constructed of rubber (including neoprene), silicone, polyurethane, other plastics, or other flexible or semi-flexible polymers (such as that sold under the trademark KRATON) or combinations of any such materials. In cases where the treatment device 20 is used in medical applications, the material comprising the flexible chamber 21 is typically also of medical grade, so that it is suitable for purposes of wound treatment (e.g., can be sterilized and does not absorb significant amounts of fluids, such as wound exudate). Preferably, the flexible chamber 21 is comprised of silicone or a silicone blend. It is to be noted that in various embodiments, the flexible chamber 21 may be constructed in whole or in part of gas-permeable materials, allowing limited amounts of air to penetrate the flexible chamber 21 so that the portion 12 of the body within the flexible chamber 21 can "breathe." In some embodiments, all portions of the flexible chamber 21 may be constructed of one type of material, such as silicone, while in other embodiments different portions of the flexible chamber 21 may be constructed of different materials, such as where one portion is constructed of rubber and another portion is constructed of silicone. This may be the case where it is desired that some portions of the flexible chamber 21 have greater strength and other portions of the flexible chamber 21 have greater flexibility. Likewise, some portions of the flexible chamber 21 may be comprised of a transparent material (to provide a viewing "window") and some portions of the flexible chamber 21 may be comprised of an opaque material. In addition, the thickness of the material comprising the flexible chamber 21 must be great enough so that the flexible chamber 21 is generally able to retain its shape when reduced pressure is present within its interior volume, while allowing the flexible chamber 21 to collapse when it is not in use. By "collapse," it is generally meant that the flexible chamber 21 may be generally flattened and folded, such as may be the case when it is necessary or desirable to store the flexible chamber 21 when it is not in use. It is also to be noted that in various embodiments, the thickness of various portions of the flexible chamber 21 may vary. This may also be the case where it is desired that some portions of the flexible chamber 21 have greater strength and other portions of the flexible chamber 21 have greater flexibility. The preferred thickness of the flexible chamber 21 is generally dependent upon the material of which the flexible chamber 21 is constructed, the size and shape of the flexible chamber 21, the level of reduced pressure anticipated within the volume of the flexible chamber 21, and the nature of the reduced pressure treatment desired.

In the illustrated embodiment, the flexible chamber 21 of the appliance 10 has an opening 23 at one end thereof that is approximately circular in shape. The opening 23 may be of almost any size or shape, as long as it does not interfere with the operation of the flexible chamber 21 and permits the object or portion of the object to be treated (the lower arm portion 12 in FIG. 1) to be positioned within the volume of the flexible chamber 21. In cases where only a portion of the object is to be treated in the flexible chamber 21, the opening 23 is generally of a size and shape to permit the sealing means to seal around the portion of the object that is approximately adjacent to the object. For example, as illustrated in FIG. 1, the opening 23 is sized and shaped to fit snugly against the portion of the lower arm 13 that is approximately adjacent to the opening 23. In this embodiment, the sealing means is comprised of a flexible sleeve 24 that is somewhat conical in shape, having an approximately cylindrical end portion 24a that is positioned approximately adjacent to the portion 13 of the arm disposed within the cylindrical end portion 24a. The flexible sleeve 24 may generally be comprised of flexible materials similar to those used to construct the flexible chamber 21. Although it is not necessary that the flexible sleeve 24 be comprised of the same material as the flexible chamber 21, it is preferred that such be the case. To assist in positioning the lower arm portions within the flexible chamber 21 and the cylindrical end portion 24a, the flexible sleeve 24 also has a gas-tight zipper 24b. Such gas-tight zippers 24b are well known in the relevant art. Other means for accomplishing the same purpose, which may be used with other embodiments of the present invention, comprise overlapping folds or flaps in the cylindrical end portion 24a (which may be held in place by hook and loop fasteners (such as VELCRO), other clamps or fasteners, or the reduced pressure within the flexible chamber 21), stretchable material that allows the opening 23 to be stretched to a greater diameter and then return to its original shape, or any combination of the same. It is to be noted that the flexible sleeve 24 may also be oriented in a direction different from that illustrated in FIG. 1. For example, the flexible sleeve 24 may extend into the flexible chamber 21, rather than away from the interior of the flexible chamber 21. In yet other embodiments where only a portion of an object is to be treated, the sealing means may be comprised of a means other than a flexible sleeve 24. For example, the opening 23 may be within the plane of the end 21a of the flexible chamber 21, and the perimeter of the opening 23 may have an inflatable cuff similar to that for the inflatable members 22a, 22b comprising the collapsible frame 22. In these embodiments, the portion of the object to be treated is positioned through the opening 23 into the interior volume of the flexible chamber 21. The inflatable cuff of this type of sealing means is then inflated using pressurized fluid from the pressurized fluid system 40 (or some other source, such as a bellows) until it fits snugly against the portion of the object (such as the lower arm portion 13 in FIG. 1) approximately adjacent to the inflatable member so that a gas-tight seal is made at that location. An example of this type of means and seal is disclosed in U.S. Pat. No. 5,425,742, the disclosure of which is incorporated herein by reference. In embodiments in which the entire object is placed within the interior volume of the flexible chamber 21 for treatment, the opening 23 is generally of a size and shape that allows the object to be placed into and removed from the flexible chamber 21. In these embodiments, the sealing means is generally used to seal the opening 23 closed in a manner that does not involve a seal against a portion of the object. For example, as illustrated and described in more detail below in connection with FIG. 6, the sealing means may be a chamber end cap portion 121c that is removably attached to a chamber body portion 121b in a manner so that the entire opening is sealed closed. In other embodiments where the object is placed entirely within the flexible chamber 21, the sealing means may also be any type of entry means that may be sealed in a gas-tight manner. Examples include caps, hatches, portals, and doors having seals similar to those disclosed in U.S. patent application Ser. No. 11/098,203, which was filed by the present inventor with the U.S. Patent and Trademark Office on Apr. 4, 2005, the disclosure of which is hereby incorporated by reference.

In the embodiment of the appliance 10 illustrated in FIG. 1, the collapsible frame 22 is comprised of generally circumferential inflatable members 22a and generally longitudinal inflatable members 22b. The circumferential inflatable members 22a generally extend around the exterior circumferential surface of the cylindrically-shaped flexible chamber 21. The longitudinal inflatable members 22b are generally disposed on the exterior surface along the longitudinal axis of the cylindrically-shaped flexible chamber 21. The circumferential inflatable members 22a and the longitudinal inflatable members 22b are in fluid communication with one another at the points where they intersect, so that fluid is permitted to flow between them. In the illustrated embodiment, the circumferential inflatable members 22a and the longitudinal inflatable members 22b are attached to the flexible chamber 21. The collapsible frame 22 is connected to the pressurized fluid system 40, which provides pressurized fluid to the collapsible frame 22, as described in more detail below. When the collapsible frame 22 is inflated with pressurized fluid, the collapsible frame 22 becomes rigid, so that it can support the flexible chamber 21 away from the object or the portion of the object to be treated (the lower arm portion 12 in FIG. 1) while the appliance 10 is in use. In other embodiments, the inflatable members 22a, 22b of the collapsible frame 22 may have almost any combination of shapes, orientations, configurations and sizes, as long as the inflatable members 22a, 22b are capable of supporting the flexible chamber 21 away from the object or portion of the object to be treated (the lower arm portion 12 in FIG. 1) while the appliance 10 is in use. For example, the collapsible frame 22 may consist of inflatable members 22a, 22b that are positioned around the circumference of the flexible chamber 21, but are also displaced somewhat along the longitudinal axis of the flexible chamber 21 in different directions so that they cross, giving rise to a series of "X-shaped" patterns. In addition, the shape of the inflatable members 22a, 22b themselves may vary. Thus, instead of having the approximately semicircular cross-section illustrated in FIG. 1, the inflatable members 22a, 22b may have a different shape or combination of shapes. For example, the inflatable members 22a, 22b (or any of them) may have an approximately circular, elliptical, square, rectangular, triangular, polygonal or other arcuate or liner cross-sectional shape or a cross-section having any combination of such shapes. Further, the size of each of the inflatable members 22a, 22b relative to each other and to the flexible chamber 21 may also vary. For example, the circumferential inflatable members 22a may have an interior cross-sectional radius of ½ inch and the longitudinal inflatable members 22b may have an interior cross-sectional radius of one inch. The collapsible frame 22 is designed to collapse in a manner similar to the flexible chamber 21, as described in more detail above. In order to collapse, the collapsible frame 22 of the illustrated embodiment is constructed of flexible or semi-flexible materials, which may be similar to those used to construct the flexible chamber 21. Although the flexible chamber 21 and the collapsible frame 22 need not be constructed of the same material, the flexible chamber 21 and the collapsible frame 22 are preferably constructed of the same material, as illustrated in FIG. 1. In addition, the material used to construct the inflatable members 22a, 22b has a thickness great enough to contain the pressurized fluid at a pressure adequate to support the flexible chamber 21 away from the portion 12 of the body to be treated while the appliance 10 is in use, but is thin enough to generally flatten and fold when the appliance 10 is not in use. The preferred material and thickness for the inflatable members 22a, 22b is generally dependent upon the size and shape of the flexible chamber 21, the size and shape of the inflatable members 22a, 22b, the pressure of the pressurized fluid used to inflate the inflatable members 22a, 22b, and the level of reduced pressure in the volume of the flexible chamber 21. As illustrated in FIG. 1, the collapsible frame 22 may be positioned on the outer surface of the flexible chamber 21. In yet other embodiments, the collapsible frame 22 may be embedded within the wall of the flexible chamber 21. In still other embodiments, the collapsible frame 22 may be positioned inside the flexible chamber 21. In all such embodiments, the collapsible frame 22 may be permanently or removably attached to the flexible chamber 21 using any suitable means. Examples of such means include hook and loop fasteners (such as VELCRO), welding, fusing, adhesives, adhesive tapes, glues, epoxies, clamps, clasps, and other fasteners and combinations of such means. In other cases, the collapsible frame 22 and the flexible chamber 21 may be fabricated as a single piece. In embodiments where the collapsible frame 22 is positioned inside the volume of the flexible chamber 21, the collapsible frame 22 may not be permanently or removably attached to the flexible chamber 21, but may instead merely rest upon the surface of the flexible chamber 21. In other embodiments of this first version of the invention, as illustrated and described below in connection with FIG. 3 through FIG. 6, the collapsible frame 122 may utilize a plurality of rigid or semi-rigid frame members 122a, 122b, 122c, rather than inflatable members 22a, 22b.

In some embodiments of this first version of the present invention, as illustrated in FIG. 1, the treatment device 20 further comprises a vacuum port 25. The vacuum port 25 is adapted to be of a size and shape so that the reduced pressure supply means 32 may be operably connected to the flexible chamber 21 by means of the vacuum port 25. When the vacuum port 25 is operably connected to the reduced pressure supply means 32, reduced pressure may be supplied to the volume within the flexible chamber 21. Although the vacuum port 25 is positioned at a location approximately at the top of one end of the flexible chamber 21 (as viewed during use) in the embodiment illustrated in FIG. 1, the vacuum port 25 may be located at other locations on the flexible chamber 21 in other embodiments, as long as the vacuum port 25 does not adversely affect the ability of the opening 23 of the flexible chamber 21 to make an operable seal with the portion 13 of the body adjacent to the opening 23, as described in more detail above, or otherwise adversely affect the operation of the flexible chamber 21. For example, the vacuum port 25 may be located near the bottom of the flexible chamber 21 (as viewed during use) so that any fluids accumulating in the flexible chamber 32 may be extracted through the reduced pressure supply means 32. Although the vacuum port 25 may be constructed of a material different from the material comprising the flexible chamber 21 in various embodiments of the invention, the vacuum port 25 is preferably constructed from the same material comprising the flexible chamber 21. In the embodiment of the treatment device 20 illustrated in FIG. 1, the vacuum port 25 is generally cylindrical in shape and is further comprised of an approximately cylindrical channel 25a that extends from the top of the vacuum port 25 to the bottom of the vacuum port 25. The vacuum port 25 of this embodiment is thus able to receive a vacuum system 30 or reduced pressure supply means 32, which are described in more detail below, adapted to be connected to this shape of vacuum port 25 and channel 25a. In other embodiments of this first version of the invention, the vacuum port 25 or the channel 25a, or both, may have different shapes and configurations as may be desired to adapt and connect the vacuum port 25 and the channel 25a to the vacuum system 30 or reduced pressure supply means 32, which are described in more detail below. In some of the embodiments comprising a vacuum port 25, the treatment device 20 may be further comprised of flow control means (not illustrated) that are operably connected to the vacuum port 25. The flow control means permit fluids to flow from the volume within the flexible chamber 21 through the vacuum port 25 to a volume (such as the reduced pressure supply means 32) outside the flexible chamber 21, but not in the opposite direction. In some of these embodiments, the flow control means may be a one-way valve that is located within the channel 25a in the vacuum port 25. Such valves are well known in the relevant art. In other embodiments of this first version of the present invention, a means of connecting the flexible chamber 21 to the reduced pressure supply means 32 (described in more detail below) may be located on the flexible chamber 21 in lieu of or in conjunction with the vacuum port 25. For example, in some embodiments, the vacuum port 25 may be combined with a variable descending diameter adapter (commonly referred to as a "Christmas tree" adapter).

In the embodiment of the first version of the present invention illustrated in FIG. 1, the reduced pressure supply source 31 of the vacuum system 30, which produces a source of reduced pressure or suction that is supplied to the flexible chamber 21, is comprised of a vacuum pump 33, a control device 34, and a filter 35. Although the preferred means of producing the reduced pressure or suction is a vacuum pump 33 in this embodiment, in other embodiments of this first version of the invention other means may be used, such as an outlet port of a centralized hospital vacuum system or a suction bulb system, which is described in more detail below. In the illustrated embodiment, predetermined amounts of suction or reduced pressure are produced by the vacuum pump 33. The vacuum pump 33 is preferably controlled by a control device 34, such as a switch or a timer that may be set to provide cyclic on/off operation of the vacuum pump 33 according to user-selected intervals. Alternatively, the vacuum pump 33 may be operated continuously without the use of a cyclical timer. In addition, in some embodiments the control device 34 may provide for separate control of the level of reduced pressure applied to the volume within the flexible chamber 21 at the portion 12 of the body to be treated and the flow rate of any fluid that may be extracted from the volume within the flexible chamber 21. In these embodiments, relatively low levels of reduced pressure may be maintained at the portion 12 of the body to be treated within the treatment device 20, while still providing for the removal of a relatively large volume of exudate from the portion 12 of the body to be treated. A filter 35, such as a micropore filter, is preferably attached to the inlet of the vacuum pump 33 to prevent potentially pathogenic microbes or aerosols from contaminating, and then being vented to atmosphere by, the vacuum pump 33. In other embodiments, the filter 35 may also be a hydrophobic filter that prevents any exudate from contaminating, and then being vented to atmosphere by, the vacuum pump 33. It is to be noted that in other embodiments of the invention, the reduced pressure supply source 31 may not have a filter 35 or a control 34 or any combination of the same.

In other embodiments of this first version of the invention, the reduced pressure supply source 31 of the vacuum system 30, may be comprised of a small, portable vacuum pump 33. In some of these embodiments, a filter 35 or a power source (not illustrated), or both, may also be contained within the housing for the portable vacuum pump 33. In these embodiments, the portable vacuum pump 33 is preferably controlled by a control device 34 that is also located within the housing for the portable vacuum pump 33, which may provide substantially the same functions as the control device 34 described above. Except for its smaller size, the portable vacuum pump 33 may operate in substantially the same manner as the vacuum pump 33 described above. Also, in these embodiments, the filter 35 may have the same structure, features, characteristics and operation, and provide substantially the same functions, as the filter 35 described above. In some of these embodiments, the filter 35 may be rigidly connected to the portable vacuum pump 33. The power source may be any source of energy currently known in the relevant art or that may be developed in the relevant art in the future that may be used to power the portable vacuum pump 33. For example, in some embodiments, the power source may be a fuel cell, battery or a standard wall electrical outlet.

In the embodiment of the first version of the invention illustrated in FIG. 1, the reduced pressure supply means 32 of the vacuum system 30, which are used to connect the reduced pressure supply source 31 to the flexible chamber 21 so that reduced pressure is supplied to the volume within the flexible chamber 21 at the portion 12 of the body to be treated is comprised of at least one tubing member 32. In this embodiment, the at least one tubing member 32 is sufficiently flexible to permit movement of the at least one tubing member 32, but is sufficiently rigid to resist constriction when reduced pressure is supplied to the flexible chamber 21 or when the location of the portion 12 of the body to be treated is such that the patient must sit or lie upon the at least one tubing member 32 or the treatment device 20 must rest upon the at least one tubing member 32. In the embodiment illustrated in FIG. 1, the at least one tubing member 32 is connected to the flexible chamber 21 by inserting one end of the at least one tubing member 32 into the channel 25a of the vacuum port 25. In this embodiment, the at least one tubing member 32 is held in place in the channel 25a by means of an adhesive. It is to be noted that in other embodiments of this first version of the invention, the at least one tubing member 32 may be connected to the vacuum port 25 using any suitable means currently known in the art or developed in the art in the future. Examples include variable descending diameter adapters (commonly referred to as "Christmas tree" adapters), luer lock fittings and adapters, clamps, and combinations of such means. Alternatively, the vacuum port 25 and the at least one tubing member 32 may be fabricated as a single piece. Similar means may be used to connect the other end of the at least one tubing member 32 to the vacuum pump 33 or other reduced pressure supply source 31 providing the reduced pressure.

Figure 2:
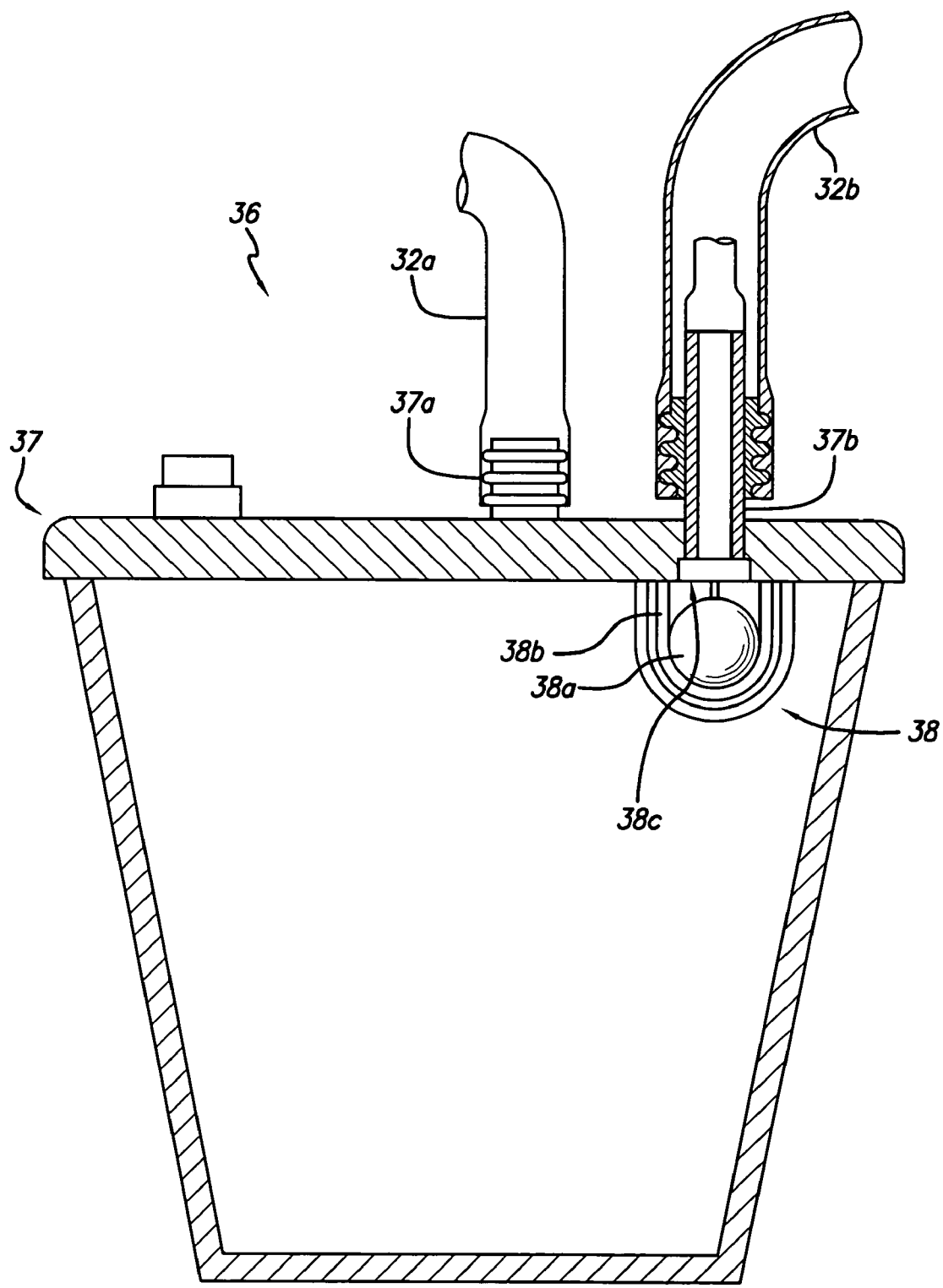
FIG. 2 is an enlarged view of an embodiment of the collection system of the vacuum system illustrated in FIG. 1.

In the embodiment illustrated in FIG. 1, the reduced pressure supply means 32 further comprise a fluid collection system, generally designated 36, that is interconnected between the suction pump 33 and the flexible chamber 21 to remove and collect any exudate that may be aspirated from the portion 12 of the body to be treated and collected within the flexible chamber 21. The reduced pressure in the flexible chamber 21 may function to actively draw fluid or exudate from the portion 12 of the body to be treated. It may be advantageous in some circumstances to locate the vacuum port 25 near the bottom of the flexible chamber 21 (as viewed while the flexible chamber 21 is in use) in order to drain this exudate so that it does not collect and fill the flexible chamber 21. In such cases, collection of exudate in a fluid collection system 36 intermediate the vacuum pump 33 and the flexible chamber 21 is desirable to prevent clogging of the vacuum pump 33. In the illustrated embodiment, the fluid collection system 36 is comprised of a fluid-impermeable collection container 37 and a shutoff mechanism 38, which are described in more detail below in connection with FIG. 2. The container 37 may be of any size and shape capable of intercepting and retaining a predetermined amount of exudate. Many examples of such containers are available in the relevant art. Referring to FIG. 2, which is an enlarged elevational cross-sectional view of the preferred embodiment of the container 37, the container 37 includes a first port 37a at the top opening of the container 37 for sealed connection to tubing member 32a, where the other end of the tubing member 32a is connected to the flexible chamber 21. The first port 37a enables suction to be applied to the flexible chamber 21 through the tubing 32a and also enables exudate from the portion 12 of the body enclosed by the flexible chamber 21 to be drained into the container 37. The container 37 provides a means for containing and temporarily storing the collected exudate. A second port 37b is also provided on the top of the container 37 to enable the application of suction from the vacuum pump 33. The second port 37b of the collection system 36 is connected to the vacuum pump 33 by tubing member 32b. The collection system 36 is sealed generally gas-tight to enable the vacuum pump 33 to supply suction to the flexible chamber 21 through the collection system 36.

The embodiment of the collection system 36 illustrated in FIG. 2 also includes a shutoff mechanism 38 for halting or inhibiting the supply of reduced pressure to the flexible chamber 21 in the event that the exudate aspirated from the portion 12 of the body to be treated exceeds a predetermined quantity. Interrupting the application of suction to the flexible chamber 21 may be desirable in some circumstances to prevent exsanguination in the unlikely event a blood 10 vessel ruptures within the portion 12 of the body to be treated during treatment. If, for example, a blood vessel ruptures within such portion 12, a shut-off mechanism would be useful to prevent the vacuum system 30 from aspirating any significant quantity of blood from the patient. In the preferred embodiment of the shutoff mechanism 38, as illustrated in FIG. 2, the shutoff mechanism 38 is a float valve assembly in the form of a ball 38a which is held and suspended within a cage 38b positioned below a valve seat 38c disposed within the opening at the top of the container below the second port 37b that will float upon the exudate and will be lifted against the valve seat 38c as the container 37 fills with exudate. When the ball 38a is firmly seated against the valve seat 38c, the float valve blocks the second port 37b and thereby shuts off the source of suction from the reduced pressure supply source 31. In other embodiments of the collection system 36, other types of mechanisms may also be employed to detect the liquid level within the container 37 in order to arrest operation of the vacuum system 30. In addition, in various embodiments of this first version of the invention, the shutoff mechanism 38 may be comprised of any means that enables the vacuum system 30 to halt the supply of reduced pressure to the flexible chamber 21 at any time that the volume of exudate from the portion 12 of the body to be treated exceeds a predetermined amount. Such means may include mechanical switches, electrical switches operably connected to the vacuum system controller 34, optical, thermal or weight sensors operably connected to the vacuum system controller 34, and any other means that are currently known in the relevant art or that may be developed in the art in the future. Such means may be located in the container 37 or in the flexible chamber 21 in various embodiments.

In some embodiments of this first version of the present invention, as illustrated in FIG. 1, the treatment device 20 further comprises a pressurized fluid port 26. The pressurized fluid port 26 is adapted to be of a size and shape so that the pressurized fluid supply means 42 may be operably connected to the collapsible frame 22 by means of the pressurized fluid port 26. When the pressurized fluid port 26 is operably connected to the pressurized fluid supply means 42, pressurized fluid may be supplied to the volume within the inflatable members 22a, 22b of the collapsible frame 22. Although the pressurized fluid port 26 is positioned at a location approximately at the top of the circumferential inflatable member 22a at one end of the collapsible frame 22 in the embodiment illustrated in FIG. 1, the pressurized fluid port 26 may be located at other locations on the collapsible frame 22 in other embodiments, as long as the pressurized fluid port 26 does not adversely affect the operation of the collapsible frame 22. In addition, there may be multiple pressurized fluid ports 26, which may be located at multiple locations on the collapsible frame 22. Although the pressurized fluid port 26 may be constructed of a material different from the material comprising the collapsible frame 22 in various embodiments of the invention, the pressurized fluid port 26 is preferably constructed from the same material comprising the collapsible frame 22. In the various embodiments of the first version of the invention that utilize an inflatable collapsible frame 22, such as is illustrated in FIG. 1, the pressurized fluid port 26 and the pressurized fluid supply means 42 may generally have substantially the same structure, features, characteristics, and operation as the various embodiments of the vacuum port 25 and reduced pressure supply means 32, respectively, illustrated and described above in connection with FIG. 1, as long as the pressurized fluid port 26 and the pressurized fluid supply means 42 are adapted to cooperate in the supply of pressurized fluid from the pressurized fluid supply source 41 to the collapsible frame 22. In some of the embodiments comprising a pressurized fluid port 26, the treatment device 20 may be further comprised of flow control means that are operably connected to the pressurized fluid port 26. The flow control means regulate the flow of pressurized fluids to and from the collapsible frame 22 through the pressurized fluid port 26. In some of these embodiments, the flow control means may be a valve that is incorporated as a part of the pressurized fluid port 26 or the pressurized fluid supply means 42. Such valves are well known in the relevant art. In other embodiments of this first version of the present invention, a means of connecting the collapsible frame 22 to the pressurized fluid supply means 42 (described in more detail below) may be located on the collapsible frame 22 in lieu of or in conjunction with the pressurized fluid port 26. For example, in some embodiments, the pressurized fluid port 26 may be combined with a variable descending diameter adapter (commonly referred to as a "Christmas tree" adapter).

In the embodiment of the first version of the present invention illustrated in FIG. 1, the pressurized fluid supply source 41 of the pressurized fluid system 40, which produces a source of pressurized air that is supplied to the collapsible frame 22, is comprised of an air compressor 43, a control device 44, and a filter 45. Although the preferred pressurized fluid is compressed air and the preferred means of producing the compressed air is an air compressor 43 in this embodiment, in other embodiments of this first version of the invention other pressurized liquids and gases, such as carbon dioxide or water, may be used instead. In addition, other pressurized fluid supply means may be used instead. For example, it may be possible to use containers of compressed fluid (such as tanks and cartridges containing compressed air or carbon dioxide), pumps (such as may be used to pressurized water), an outlet port of a centralized hospital compressed gas system, or a bellows-type system. In the illustrated embodiment, predetermined amounts of pressurized fluid are produced by the air compressor 43. The air compressor 43 is preferably controlled by a control device 44, such as a switch or a timer that may be set to provide cyclic on/off operation of the air compressor 43 according to user-selected intervals. Alternatively, the air compressor 43 may be operated continuously without the use of a cyclical timer. In addition, in some embodiments the control device 44 may provide for separate control of the level of pressurized fluid applied to the volume within the inflatable members 22a, 22b of the collapsible frame 22. For example, the control device 44 may also be operably connected to a pressure sensor located on or within the collapsible frame 22, so that the control device 44 halts operation of the air compressor 43 when the pressure within the collapsible frame 22 reaches a predetermined level and turns the air compressor 43 on when the pressure within the collapsible frame 22 falls below a predetermined level. A filter 45, such as a micropore filter, is preferably attached to the outlet of the air compressor 43 to prevent contaminants from being transferred from the air compressor 43 to the interior volume of the collapsible frame 22. In other embodiments, the filter 45 may also be a hydrophobic filter that prevents any moisture from being transferred from the air compressor 43 to the interior volume of the collapsible frame 22. It is to be noted that in other embodiments of the invention, the pressurized fluid supply source 41 may not have a filter 45 or a control 44 or any combination of the same. In other embodiments of this first version of the invention, the pressurized fluid supply source 41 of the pressurized fluid system 40 may be comprised of a small, portable air compressor 43 or container of compressed fluid, which may also contain a filter 45 or a control device 44 or both within the same housing for the air compressor 43 or container. Except for its smaller size, the portable air compressor 43, and the filter 45 and controller 44, if any, may operate in substantially the same manner as the air compressor 43, filter 45, and controller 44, respectively, described above. The air compressor 43 may also comprise a power source, such as a fuel cell, battery or a standard wall electrical outlet. In other embodiments, the air compressor 43 and the vacuum pump 33 may operate as an integrated unit contained in a single enclosure. In some of these embodiments, the air compressor 43 and the vacuum pump 33 may be driven by the same mechanical source (such as an electric motor).

In the embodiment of the first version of the invention illustrated in FIG. 1, the pressurized fluid supply means 42 of the pressurized fluid system 40, which are used to connect the pressurized fluid supply source 41 to the collapsible frame 22 so that pressurized fluid is supplied to the volume within the inflatable members 22a, 22b of the collapsible frame 22 is comprised of at least one tubing member 42. In this embodiment, the at least one tubing member 42 is sufficiently flexible to permit movement of the at least one tubing member 42, but is sufficiently rigid to resist expansion when pressurized fluid is supplied to the collapsible frame 22 and is sufficiently rigid to resist constriction when the location of the portion 12 of the body to be treated is such that the patient must sit or lie upon the at least one tubing member 42 or the treatment device 20 must rest upon the at least one tubing member 42. In the embodiment illustrated in FIG. 1, the at least one tubing member 42 is connected to the collapsible frame 22 by inserting one end of the at least one tubing member 42 into a channel 26a in the pressurized fluid port 26. In this embodiment, the at least one tubing member 42 is held in place in the channel 26a by means of an adhesive. It is to be noted that in other embodiments of this first version of the invention, the at least one tubing member 42 may be connected to the pressurized fluid port 26 using any suitable means currently known in the relevant art or developed in the relevant art in the future. Examples include variable descending diameter adapters (commonly referred to as "Christmas tree" adapters), luer lock fittings and adapters, clamps, and combinations of such means. Alternatively, the pressurized fluid port 26 and the at least one tubing member 42 may be fabricated as a single piece. Similar means or other means, which are currently known in the relevant art or may be developed in the relevant art in the future, may be used to connect the other end of the at least one tubing member 42 to the air compressor 43 or other reduced pressure supply source 41 providing the reduced pressure.

In the embodiment of the first version of the present invention illustrated in FIG. 1, the appliance 10 is also comprised of a drainage system 50. In the illustrated embodiment, the drainage system 50 is further comprised of an overlay 51, wound packing means 52, and draining means 53. The overlay 51, which is described in more detail below, may generally be used to cover a wound 14 and collect any exudate aspirated from the wound 14. This may be desirable to prevent contamination of the flexible chamber 21 in cases where the portion of the body to be treated 12 has a wound 14 that is expected to aspirate significant quantities of exudate during the treatment process. The wound packing means 52, which is also described in more detail below, may be placed into or over the wound 14 to assist in healing of the wound 14. The draining means 53, which are also described in more detail below, may be used to remove exudate aspirated by the wound 14 from the overlay 51 and the treatment device 20. It is to be noted that the drainage system 50 need not be used in every embodiment of the present invention. It is also to be noted that in some embodiments, only the overlay 51 and draining means 53 may be used, while in other embodiments only the overlay 51 and wound packing means 52 may be used. In still other embodiments, only the wound packing means 52 and draining means 53 may be utilized.

The overlay 51, which is constructed of a semi-permeable or impermeable material, is generally adapted to be of a size and shape to cover the wound 14. Overlays 51 that may be used for this purpose are well known in the art. Examples of such overlays are generally disclosed in U.S. patent application Ser. No. 10/652,100 (filed on Aug. 28, 2003), Ser. No. 11/026,733 (filed on Dec. 30, 2004), Ser. No. 11/064,813 (filed on Feb. 24, 2005), Ser. No. 11/095,859 (filed by the present inventor with others on Mar. 31, 2005) Ser. No. 11/098,265 (filed on Apr. 4, 2005), and Ser. No. 11/098,203 (filed on Apr. 4, 2005), which were filed by the present inventor with the U.S. Patent and Trademark Office. The disclosures of these U.S. patent applications are incorporated herein by reference. The overlay 51 may be comprised of rigid, semi-rigid, or flexible materials or combinations of such materials. Where the overlay 51 is constructed of a semi-permeable material, the reduced pressure within the flexible chamber 21 is also applied to the wound 14 under the overlay 51, but exudate aspirated from the wound 14 is generally not able to pass through the overlay 51 to the interior volume of the flexible chamber 21. Where the overlay 51 is constructed of a fluid (liquid and gas) impermeable material, the reduced pressure within the flexible chamber 21 is not generally applied to the wound 14 under the overlay 51, and exudate aspirated from the wound 14 is generally not able to pass through the overlay 51 to the interior volume of the flexible chamber 21. In such cases, it may be possible to provide reduced pressure treatment to some parts of the portion 12 of the body within the volume of the flexible chamber 21, but not others, such as the wound 14 covered by a rigid, fluid-impermeable overlay 51. The overlay 51 may be removably attached to the tissue of the patient surrounding the wound 14 using any suitable means currently known in the relevant art or that may be developed in the relevant art in the future, such as adhesives, adhesive tapes, reduced pressure, means disclosed in any of the U.S. patent applications referenced above in this paragraph, or other means or combinations of any such means. It is to be noted that the overlay 51 may be used in other embodiments of the present invention with or without drainage means 53 or wound packing means 52.

In some embodiments of this first version of the invention, the drainage system 50 further comprises tissue protection means (not illustrated) to protect and strengthen the surface tissue surrounding the wound 14 that is adjacent to the overlay 51. The tissue protection means protects such tissue by preventing abrasion and maceration of the tissue. Preferably, the tissue protection means is a hydrocolloid material, such as COLOPAST Hydrocolloid 2655, anhydrous lanoline, or any combination of such hydrocolloid materials. More preferably, the tissue protection means is COLOPAST Hydrocolloid 2655. The tissue protection means may be applied to the body tissue to be protected, or it may be applied to the surface of the overlay 51 that is to be in contact with the body tissue, or both, prior to placing the overlay 51 over the wound 14. It is to be noted that application of the tissue protection means to the body tissue that is adjacent to the overlay 51 surrounding the wound 14 may only entail application of the tissue protection means to the parts of the body tissue adjacent to the overlay 51 that require such protection.

In the embodiment of the first version of the invention illustrated in FIG. 1, the drainage system 50 is further comprised of wound packing means 52, which is placed in the area of the wound 14 under the overlay 51. In this embodiment, the overlay 51 may be used to hold the wound packing means 52 in place. It is to be noted that the wound packing means 52 may be used with other embodiments of the present invention with or without drainage means 53 or an overlay 51. In the illustrated embodiment, the overlay 51 is placed over the wound 14 and the wound packing means 52 when the overlay 51 is positioned on the surface of the body at the site of the wound 14. In some embodiments of this first version of the invention, the wound packing means 52 may be placed within the wound 14 to prevent overgrowth of the tissue in the area of the wound 14. For example, and preferably in these cases, the wound packing means 52 may be comprised of absorbent dressings, antiseptic dressings, nonadherent dressings, water dressings, or combinations of such dressings. More preferably, the wound packing means 52 may be comprised of gauze or cotton or any combination of gauze and cotton. In still other embodiments of this first version of the invention, the wound packing means 52 may be comprised of an absorbable matrix adapted to encourage growth of the tissue in the area of the wound 14 into the matrix. In these embodiments, the absorbable matrix (as wound packing means 52) is constructed of an absorbable material that is absorbed into the epithelial and subcutaneous tissue in the wound 14 as the wound 14 heals. The matrix (as wound packing means 52) may vary in thickness and rigidity, and it may be desirable to use a spongy absorbable material for the patient's comfort. The matrix (as wound packing means 52) may also be perforated and constructed in a sponge-type or foam-type structure to enhance fluid flow and to reduce the weight of the matrix. Because of the absorbable nature of the absorbable matrix (as wound packing means 52), the matrix should require less frequent changing than other dressing types during the treatment process. In other circumstances, the matrix (as wound packing means 52) may not need to be changed at all during the treatment process. In some embodiments of this first version of the invention, the absorbable matrix (as wound packing means 52) may be comprised of collagens or other absorbable materials or combinations of all such materials. U.S. patent application Ser. No. 10/652,100, which was filed by the present inventor with the U.S. Patent and Trademark Office on Aug. 28, 2003, and is hereby incorporated by reference, also discloses various embodiments of an absorbable matrix that may be utilized with various embodiments of this first version of the present invention. It is to be noted that wound packing means 52 may also be utilized in other versions of the invention.

In the embodiment of the first version of the invention illustrated in FIG. 1, the drainage system 50 of the appliance 10 is also comprised of draining means 53. In this embodiment, the draining means 53 are further comprised of a bottom drain portion 53a extending into the area of the wound 14 under the overlay 51 from a top drain portion 53b positioned outside the volume under the overlay 51 at the area of the wound 14. In the illustrated embodiment, the top drain portion 53b is operably connected to the reduced pressure supply source 31 so that the draining means 53 are in fluid communication with the reduced pressure supply source 31 and reduced pressure is supplied to the volume under the overlay 51 in the area of the wound 14 by the draining means 53. It is to be noted that the reduced pressure supply source 31 may include another filter 35', which may have substantially the same structure, features, characteristics and operation as filter 35. In this embodiment, valves 54a, 54b are operably positioned in the top drain portion 53b to regulate flow of reduced pressure and exudate within the drainage system 50. In addition, a collection system 56 is operably positioned within the drainage system 50. In various embodiments, the collection system 56 may have substantially the same structure, features, characteristics and operation as various embodiments of the collection system 36 that is part of the vacuum system 30. It is to be noted, however, that the collection system 56 need not be present in all embodiments of the present invention. Thus, when valve 54a is closed and valve 54b is open, any exudate aspirated from the wound 14 is collected by the draining means 53 from the volume under the overlay 51 and flows into the collection system 56. In embodiments without a collection system 56, the exudate may flow to any other receptacle or means for disposing of the exudate. In these cases, there is no source providing reduced pressure to the volume under the overlay 51 at the site of the wound 14. When valve 54a is open and valve 54b is closed, any exudate aspirated from the wound 14 is also collected by the draining means 53 from the volume under the overlay 51 and flows into the collection system 56. In this case, however, reduced pressure is supplied by the reduced pressure supply source 31 through the draining means 53 to the volume under the overlay 51 at the site of the wound 14. This reduced pressure may act to draw exudate aspirated from the wound 14 into the draining means 53 (and thus into the collection system 56). It is to be noted that in other embodiments the drainage system 50 may not have any valves 54a, 54b, so that the draining means 53 is connected directly to the reduced pressure supply source 31. In yet other embodiments, the draining means 53 may not be connected to the reduced pressure supply source 31 at all, so that exudate collected from the volume under the overlay 51 may flow directly to a receptacle (such as the collection system 56) or other means for disposing of the exudate. In the latter cases, there is no source providing reduced pressure to the volume under the overlay 51 at the site of the wound 14.

In the illustrated embodiment, the top drain portion 53b passes through and is attached to a drainage port 27 located on the flexible chamber 21. The drainage port 27 may generally have substantially the same structure, features, characteristics and operation as the vacuum port 25 described above. In addition, the drainage port 27 may be positioned on the flexible chamber 21 in substantially the same manner as the vacuum port 25, as described above. In this embodiment, the top drain portion 53b may be comprised of two portions, where one portion is attached to the opening of the drainage port 27 that is inside the flexible chamber 21 and the other portion is attached to the opening of the drainage port 27 that is outside the flexible chamber 21. In some embodiments, the top drain portion 53b may be permanently or removably attached to the interior surface of the opening of the drainage port 27 using any suitable means, such as an adhesive, or by the top drain portion 53b having a shape adapted so that all or a portion of it fits tightly against all or a portion of the interior surface of the opening in the drainage port 27. The suction drain system disclosed in U.S. patent application Ser. No. 11/026,733, entitled "Improved Reduced Pressure Wound Treatment Appliance," which was filed by the present inventor with the U.S. Patent and Trademark Office on Dec. 30, 2004, may also be used in conjunction with the present invention. The disclosure of this U.S. patent application is incorporated herein by reference. In yet other embodiments, the top drain portion 53b may pass through the opening 23 in the flexible chamber 21 in a manner so that the sealing means (the flexible sleeve 24) provides a gas-tight seal with the top drain portion 53b as well as the portion 13 of the body adjacent to the flexible sleeve 24. In yet other embodiments, the drainage port 27 may be comprised of a different connecting means, such as a variable descending diameter adapter (commonly referred to as a "Christmas tree" adapter), clamp, fastening collar, luer lock fitting and adapter, or other fastener or combination thereof. In yet other embodiments, the top drain portion 53b may be fused or welded to the drainage port 27 or another portion of the flexible chamber 21. In still other embodiments, the top drain portion 53b may be fabricated as a part of the flexible chamber 21. In each case, the top drain portion 53b may pass through the flexible chamber 21 at any point that is convenient, as long as the operation of the treatment device 20 is not adversely affected.

In the embodiment illustrated in FIG. 1, the top drain portion 53b and the bottom drain portion 53a of the draining means 53 are comprised of polymer tubing that is flexible enough to allow the tubing to easily bend, but rigid enough to prevent the tubing from collapsing during use. In other embodiments, portions of the top drain portion 53b and the bottom drain portion 53a of the draining means 53 may be comprised of other materials, such as flexible or semi-rigid polymers, plastics, rubber, silicone, or combinations of such materials. In yet other embodiments, the draining means 53 may have different cross-sectional shapes, such as elliptical, square, rectangular, pentagonal, hexagonal, or other shapes. In still other embodiments, the bottom drain portion 53a of the draining means 53 may be further comprised of wound suction means (not illustrated) that may be used to remove debris, exudate and other matter from the wound 14. For example, the wound suction means may be comprised of a distal end portion (not illustrated) of the tubing comprising the bottom drain portion 53a having a plurality of perforations in the surface of the distal end portion. The suction drain system disclosed in U.S. patent application Ser. No. 11/026,733, entitled "Improved Reduced Pressure Wound Treatment Appliance," which was filed by the present inventor with the U.S. Patent and Trademark Office on Dec. 30, 2004, discloses examples of this type of wound suction means. The disclosure of this U.S. patent application is incorporated herein by reference. In the illustrated embodiment, the bottom drain portion 53a of the draining means 53 extends into the interior volume of the wound packing means 52. In this embodiment, the wound packing means 52 and the draining means 53 may be fabricated by snaking the distal end portion of the bottom drain portion 53a of the draining means 53 through an internal passageway in the wound packing means 52, such as by pulling the distal end portion of the draining means 53 through the passageway using forceps. Alternatively, the wound packing means 52 and the draining means 53 may be manufactured as a single piece in sterile conditions and then be stored in an aseptic package until ready for use. In other embodiments, the distal end portion of the draining means 53 may be placed adjacent or close to the wound packing means 52 in the area of the wound 14. The preferred means of placement of the draining means 53 relative to the wound packing means 52 is dependent upon the type of wound 14, the type of wound packing means 52, and the type of treatment desired.

In the embodiment of the present invention illustrated in FIG. 1, the treatment device 20 is further comprised of a treatment port 28. The treatment port 28 allows for access to the volume within the flexible chamber 21 for purposes of attending to the object or portion of the object (the portion 12 of the lower arm in FIG. 1) within the volume of the flexible chamber 21. For example, the treatment port 28 may be used to provide treatment to the lower arm portion 12 by injecting medical gases, as well as treatment devices and related electrical, hydraulic and other supply lines into the volume of the flexible chamber 21. The treatment port 28 may be of almost any size and shape, as long as it does not adversely interfere with the operation of the appliance 10. Thus, in some embodiments, the treatment port 28 may have substantially the same structure, features, characteristics and operation as the vacuum port 25, the pressurized fluid port 26, or the drainage port 27 described in more detail above, or any other type of gas-tight port currently known in the relevant art or developed in the relevant art in the future. In such embodiments, supply lines may be used in connection with the treatment port 28 in substantially the same manner that the reduced pressure supply means 32 is used with the vacuum port 25, the pressurized fluid supply means 42 is used with the pressurized fluid port 26, or the draining means 53 is used with the drainage port 27, or any combination thereof. In other embodiments, the treatment port 28 may be larger, as illustrated in FIG. 1. In addition, the treatment port 28 may be located at almost any position on the flexible chamber 21, as long as it does not adversely interfere with the operation of the appliance 10. Further, the treatment port 28 may have almost any structure that allows it to remain gas-tight while the appliance 10 is in use. For example, as illustrated in FIG. 1, the treatment port 28 is comprised of a port body 28a that is attached to the flexible chamber 21 and a port cap 28b, which is removably attached to the port body 28a. Any means suitable to produce a gas-tight seal may be used to removably attach the port cap 28b to the port body 28a. For example, an o-ring/groove seal may be used. Other suitable means are disclosed in U.S. patent application Ser. No. 11/098,203, which was filed by the present inventor with the U.S. Patent and Trademark Office on Apr. 4, 2005, the disclosure of which is hereby incorporated by reference. In yet other embodiments, the treatment port 28 may be relatively large, as illustrated in FIG. 1, and have additional ports similar to the vacuum port 25, the pressurized fluid port 26, or the drainage port 27, other types of ports, or any combination thereof positioned on the port body 28a, the port cap 28b, or both. It is to be noted that in various embodiments of the present invention, there may be more than one treatment port 28 or no treatment port 28. In addition, where there is more than one treatment port 28, the treatment ports 28 may vary in size and structure. The treatment port 28 may be constructed of any suitable rigid, semi-rigid or flexible material or combinations of such materials. For example, the treatment port 28 may be constructed in whole or in part of metals, ceramics, glasses, silicone, rubber (including neoprene), polycarbonate, polyvinyl chloride, polyurethane, or other polymers or combinations of any such materials.

In the embodiment of the present invention illustrated in FIG. 1, the treatment device 20 is further comprised of a forced entry treatment system 60. In the illustrated embodiment, the forced entry treatment system 60 is further comprised of a forced entry supply source, illustrated schematically and generally designated 61, forced entry supply means 62, and venting means 63. The forced entry treatment system 60 generally provides for introducing ancillary fluids into the volume within the flexible chamber 21. For example, air or other gas that is heated or cooled may be introduced by the forced entry treatment system 60 into the volume within the flexible chamber 21 in order to raise or lower, respectively, the temperature of the object or portion of the object to be treated (the lower arm portion 12 in FIG. 1). As another example, ionized gases and dyes may be introduced by the forced entry treatment system 60 into the volume within the flexible chamber 21. Thus, the forced entry supply source 61 may be comprised of any type of equipment that is related to providing the forced entry treatment. For example, the forced air supply source 61 may be comprised of equipment to heat or cool (or both) gases or liquids or both and cause such gases or liquids to flow from the forced entry supply source 61 through the forced entry supply means 62 to the flexible chamber 21. Equipment of this type, such as heat exchangers, boilers and heating elements, refrigeration coils, and blowers and pumps are well known in the relevant art. The forced entry supply means 62 may be comprised of any suitable means currently known in the relevant art or the may be developed in the relevant art in the future. For example, the forced entry supply means 62 may be comprised of one or more tubing members similar to those used for the reduced pressure supply means 32, the pressurized fluid supply means 42, or the draining means 53, as described above. As another example, the forced entry supply means 62 may be comprised of ducts, which are constructed from any suitable material, such as metals, woods, plastics, or other polymers or combinations of any such materials. The forced entry supply means 62 is connected to the flexible chamber 21 by means of a forced entry port 29, which may be of almost any size and shape, as long as it does not adversely interfere with the operation of the appliance 10. Thus, in some embodiments, the forced entry port 29 may have substantially the same structure, features, characteristics and operation as the vacuum port 25, the pressurized fluid port 26, or the drainage port 27 described in more detail above, or any other type of gas-tight port currently known in the relevant art or developed in the relevant art in the future. In such embodiments, forced entry supply means 62 may be used in connection with the forced entry port 29 in substantially the same manner that the reduced pressure supply means 32 is used with the vacuum port 25, the pressurized fluid supply means 42 is used with the pressurized fluid port 26, or the draining means 53 is used with the drainage port 27, or any combination thereof. In other embodiments, the forced entry port 29 may be larger. In addition, the forced entry port 29 may be located at almost any position on the flexible chamber 21, as long as it does not adversely interfere with the operation of the appliance 10. Further, the forced entry port 29 may have almost any structure that allows it to remain gas-tight while the appliance 10 is in use. It is to be noted that in various embodiments of the present invention, there may be more than one forced entry port 29 or no forced entry port 29. In addition, where there is more than one forced entry port 29, the forced entry ports 29 may vary in size and structure. The venting means 63 may generally be used to vent fluids that are introduced into the interior volume of the flexible chamber 21 by the forced entry supply source 61 and forced entry supply means 62. In the illustrated embodiment, the venting means 63 is further comprised of a vent member 63a and a valve 63b, which regulates the flow of fluid from the interior volume of the flexible chamber 21 through the vent member 63a. The venting means 63 may discharge fluid to the ambient atmosphere or to a suitable receptacle or return the fluid to the forced entry supply source 61 for processing, recycle or some other purpose. It is to be noted that in some embodiments, the appliance 10 may not include a forced entry treatment system 60 or may have more than one forced entry treatment system 60. In other embodiments, the forced entry treatment system 60 may not include any venting means 63 or may have more than one venting means 63.

The present invention also includes a method of administering reduced pressure treatment to an object or a portion of an object using various embodiments of the first version of the present invention, as described above and illustrated in connection with FIG. 1 and FIG. 2. Generally, the method comprises the following steps. First, an appliance 10 for administering reduced pressure to the object or portion of the object (the lower arm portion 12 in FIG. 1) is provided. Second, the appliance 10 is positioned for use, so that the flexible chamber 21 and collapsible frame 22 are in an extended state. For example, where the collapsible frame 22 is further comprised of at least one inflatable member 22a, 22b, and the appliance 10 is further comprised of a pressurized fluid supply source 41 and pressurized fluid supply means 42 to operably connect the at least one inflatable member 22a, 22b to the pressurized fluid supply source 41, the at least one inflatable member 22a, 22b is inflated to the desired pressure with pressurized fluid using the pressurized fluid supply source 41 and pressurized fluid supply means 42. Third, the object or portion of the object to be treated (the lower arm portion 12 in FIG. 1) is positioned relative to the appliance 10 so that the object or portion of the object to be treated (the lower arm portion 12 in FIG. 1) is positioned within the volume of the flexible chamber 21. In the embodiment illustrated in FIG. 1, the lower arm portion 12 is inserted through the opening 23 into the interior volume of the flexible chamber 21. Fourth, the opening 23 of the flexible chamber 21 is sealed using the sealing means (the flexible sleeve 24 in FIG. 1), so that reduced pressure may be maintained in the volume within the flexible chamber 21. Fifth, the flexible chamber 21 is operably connected with the reduced pressure supply source 31 using the reduced pressure supply means 32 so that reduced pressure is supplied to the volume within the flexible chamber 21. It is to be noted that the fifth step may be also performed before either the second, third or fourth step described above. In the preferred embodiments of this first version of the invention involving medical treatment, the reduced pressure maintained in the volume within the flexible chamber 21 at the portion 12 of the body to be treated is in the range from approximately 20 mm of Hg below atmospheric pressure to approximately 125 mm of Hg below atmospheric pressure. In yet other embodiments, the reduced pressure is applied to the flexible chamber 21 in a cyclic nature, the cyclic nature providing alternating time periods of application of reduced pressure and non-application of reduced pressure. Sixth, the reduced pressure is maintained in the volume within the flexible chamber 21 until the object or portion of the object being treated (the lower arm portion 12 in FIG. 1) has progressed toward a selected stage of treatment. Seventh, the object or portion of the object to be treated (the lower arm portion 12 in FIG. 1) is removed from the appliance 10 after the selected stage of treatment has been reached and the reduced pressure within the volume of the flexible chamber 21 has been released. Eighth, the appliance 10 is placed in its collapsed state. In the embodiment illustrated in FIG. 1, this involves the deflation of the at least one inflatable member 22a, 22b and folding the collapsible frame 22 and the flexible chamber 21. In embodiments comprising a drainage system 50, the method also includes the step of positioning the wound packing means 52 (if any) in the wound 14, positioning the draining means 53 (if any) in or over the wound 14 (or in the wound packing means 52), positioning the overlay 51 over the wound 14 (and wound packing means 52 and draining means 53, if any), and connecting the draining means 53 to the reduced pressure supply source 31 and the collection system 56, if desired. In embodiments comprising a forced entry treatment system 60, the method also includes the step of positioning the forced 25 entry supply source 61 in proximity to the treatment device 20, connecting the forced entry supply means 62 to the forced entry supply source 61 and the flexible chamber 21, and operating the forced entry treatment system 60 until the desired force entry treatment is completed.

Another embodiment of the first version of the present invention is illustrated in FIG. 3 through FIG. 6. In this embodiment, the treatment device 120 is also comprised of a flexible chamber 121 and a collapsible frame 122, but the collapsible frame 122 is comprised of a plurality of rigid or semi-rigid frame members 122a, 122b, 122c and frame member connecting means, which are described in more detail below. The frame member connecting means are used to connect the plurality of rigid or semi-rigid frame members 122a, 122b, 122c together in a manner so that the plurality of rigid or semi-rigid frame members 122a, 122b, 122c may be extended when the appliance 110 is in use and collapsed when the appliance 110 is not in use. In the illustrated embodiment, the flexible chamber 121 is constructed of a transparent material so that the collapsible frame 122 may be viewed from outside the flexible chamber 121. Also in the illustrated embodiment, the flexible chamber 121 and the sealing means 124 may have substantially the same structure, features, characteristics and operation as the various embodiments of the flexible chamber 21 and the sealing means 124, respectively, described above and illustrated in connection with FIG. 1. In this embodiment, however, the flexible chamber 121 is generally comprised of a chamber body portion 121*b*, a flexible sleeve 124 (as sealing means) having an opening 123 that is positioned at one end 121*a* of the chamber body portion 121*b*, and a chamber end cap portion 121*c* that is removably attached to the other end of the chamber body portion 121*b*. Generally, the chamber end cap portion 121*c* is removed from the chamber body portion 121*b* so that the collapsible frame 122 may be inserted into the chamber body portion 121*b*. After the collapsible frame 122 is inserted into the chamber body portion 121*b*, the chamber end cap portion 121*c* is attached to the chamber body portion 121*b* by end cap attachment means. The end cap attachment means may be any suitable means that permits the chamber end cap portion 121*c* to be detached from the chamber body portion 121*b* and to be re-attached in a manner that provides a hermetic seal between the chamber end cap portion 121*c* and the chamber body portion 121*b*, so that reduced pressure may be maintained within the volume of the flexible chamber 121 while the appliance 110 is in use. For example, the end cap attachment means may include gas-tight zippers, hook and loop fasteners, or other fasteners or combinations of such fasteners.

In the embodiment of the present invention illustrated in FIG. 3 through FIG. 6, the collapsible frame 122 is generally comprised of a plurality of rigid or semi-rigid frame members 122*b* that extend longitudinally, rigid or semi-rigid frame members 122*a* that are approximately circular in shape and positioned at the ends of the collapsible frame 122, a rigid or semi-rigid frame member 122*c* that supports the chamber end cap portion 121*c*, and frame member connecting means, which are described in more detail below. In the illustrated embodiment, the plurality of rigid or semi-rigid frame members 122*a*, 122*b*, 122*c* are comprised of rigid or semi-rigid materials, so that they are generally capable of maintaining their shape and supporting the flexible chamber 121 away from the object or portion of the object to be treated (the lower arm portion 112 in FIG. 3) while reduced pressure is present within the volume inside the flexible chamber 121. Examples of such materials include wood, metal, ceramics, plastics and other rigid or semi-rigid polymers (such as polyvinyl chloride and polycarbonate) and combinations of such materials. The frame member connecting means may be comprised of any means suitable for connecting the rigid or semi-rigid frame members 122*a*, 122*b*, 122*c* together in a manner that allows the rigid or semi-rigid frame members 122*a*, 122*b*, 122*c* to pivot, rotate or otherwise move in a manner that permits the rigid or semi-rigid frame members 122*a*, 122*b*, 122*c* to collapse and to extend when desired. For example, as illustrated in FIG. 5, the frame member connecting means may be comprised of a rivet 122*d* that is used to join the ends of the rigid or semi-rigid frame members 122*b* together. The frame member connecting means may also include additional features to enable the rigid or semi-rigid frame members 122*a*, 122*b*, 122*c* to retain the extended position when desired. For example, as illustrated in FIG. 5, the rigid or semi-rigid frame members 122*b* are also comprised of a tab portion 122*e*, a raised portion 122*f*, and an indented portion 122*g*. In this embodiment, the tab portion 122*e* rests against the surface of the adjoining rigid or semi-rigid frame member 122*b* when the rigid or semi-rigid frame members 122*b* are fully extended. In addition, the raised portion 122*f*, which is positioned in the indented portion 122*g* when the rigid or semi-rigid frame members 122*b* are fully extended, acts to hold the collapsible frame 122 in place in the extended position. It is to be noted that the frame member connecting means may comprise other means in other embodiments of the present invention. For example, the frame member connecting means may include pins, nut/bolt combinations, dowels, screws, hinges, or other connectors or combinations of such means.

Figure 3:
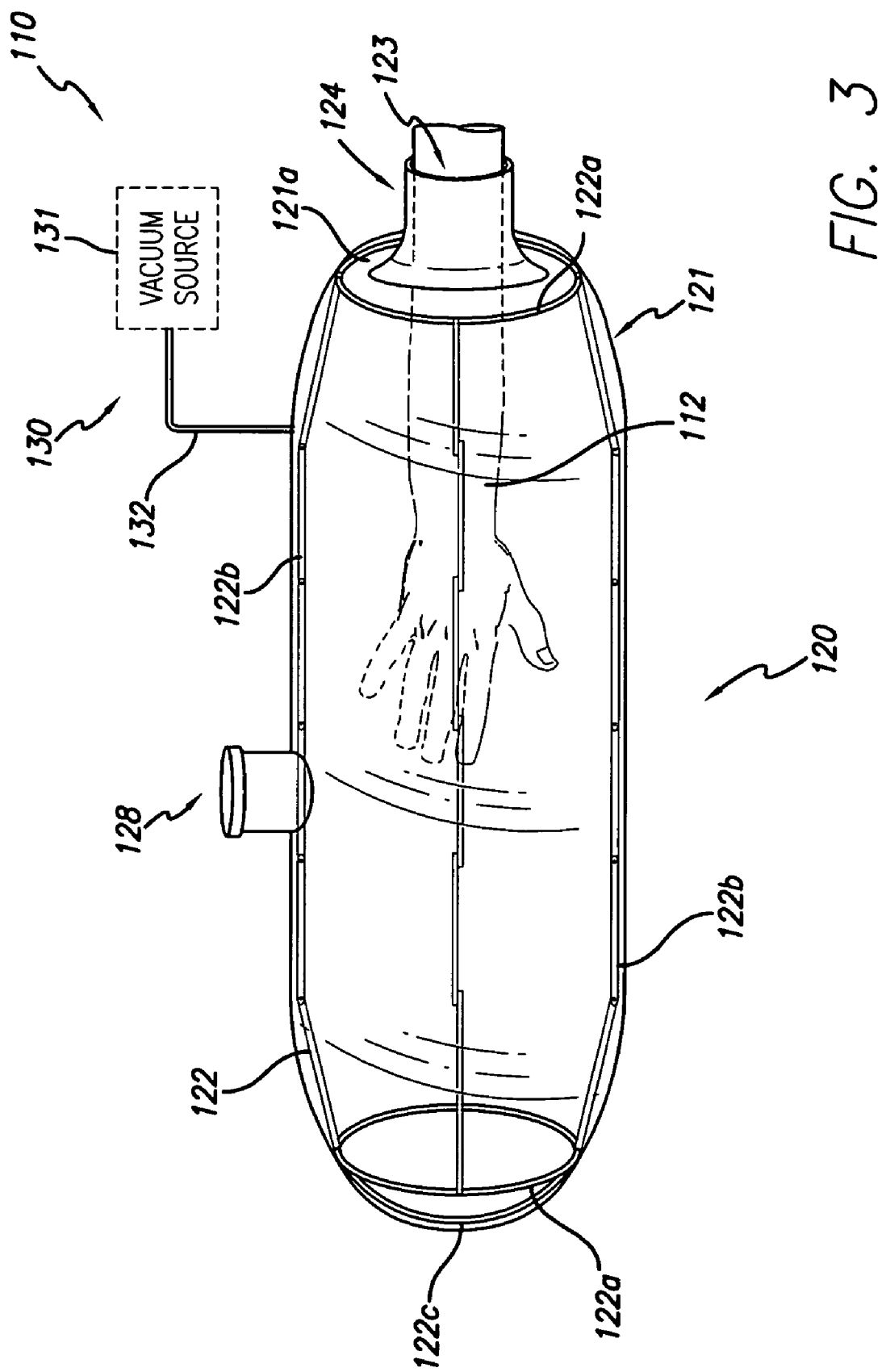
FIG. 3 is a view of an appliance comprising the present invention, in which an embodiment of a treatment device, shown in perspective view, encloses the lower arm portion of a patient, and in which an embodiment of a vacuum system, depicted generally and shown partially in schematic elevation view, provides reduced pressure to the treatment device.

In the embodiment of the collapsible frame 122 illustrated in FIG. 3 through FIG. 6, the collapsible frame 122 is approximately cylindrical in shape when it is fully extended, as illustrated in FIG. 3. When the collapsible frame 122 is not in use and sufficient force is exerted on the various rigid or semi-rigid frame members 122*a*, 122*b*, 122*c* comprising the collapsible frame 122, the collapsible frame 122 collapses in an "accordion" fashion, as illustrated in FIG. 4, in which the collapsible frame 122 is shown in a partially collapsed state. It is to be noted that the collapsible frame 122 may be of almost any shape and size necessary to adapt to the shape of the flexible chamber 121. In addition, it is to be noted that the plurality of rigid or semi-rigid frame members 122*a*, 122*b*, 122*c* comprising the collapsible frame 122 may be arranged in many different structural patterns and have many different ways in which to collapse and extend. Further, the frame member connecting means may include many different means of connecting the rigid or semi-rigid frame members 122*a*, 122*b*, 122*c* comprising the collapsible frame 122. All such sizes, shapes, structural patterns, means of collapse and extension, and connecting means are encompassed by the present invention, as set forth in the appended claims. It is also to be noted that all of the features of the appliance 10 described above and illustrated in connection with FIG. 1 may also be utilized with the appliance 110 illustrated in FIG. 3 through FIG. 6. For example, the appliance 110 generally comprises a vacuum system 130 having a reduced pressure supply source 131 and reduced pressure supply means 132, which may have substantially the same structure, features, characteristics and operation as the various embodiments of the vacuum system 30 of appliance 10. Finally, it is to be noted that in operation of the appliance 110, the step of positioning the appliance 110 for use further comprises the steps of extending the rigid or semi-rigid frame members 122*a*, 122*b*, 122*c* comprising the collapsible frame 122 to their extended state.

Figure 8:
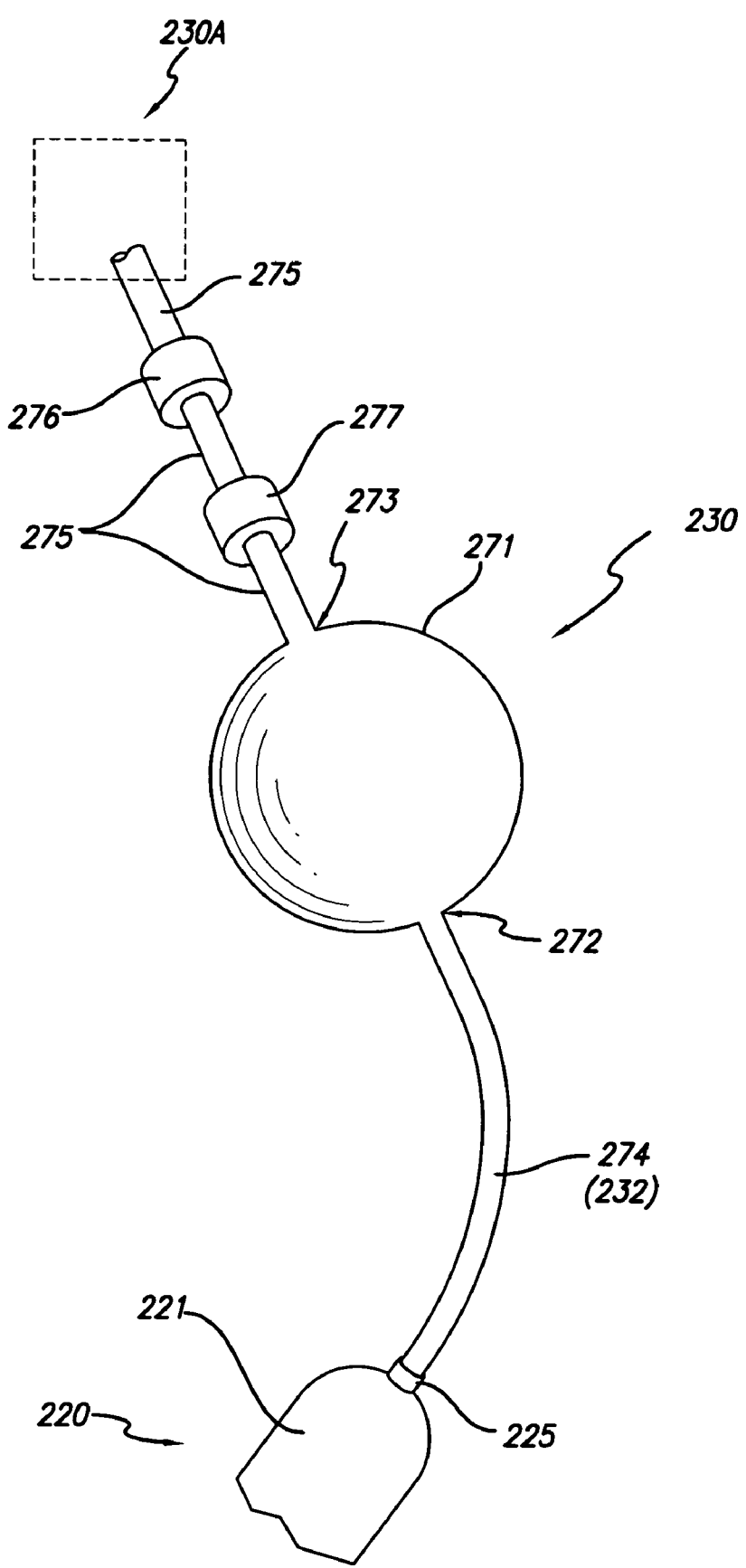
FIG. 8 is a perspective view of an embodiment of a suction bulb system that may be used as a source of reduced pressure or fluid collection or both, and a supplemental vacuum system, depicted generally and shown in schematic elevation view.

An embodiment of a second version of the present invention is illustrated in FIG. 7. In this embodiment, an appliance 210 is disclosed that is generally comprised of a treatment device 220, a vacuum system 230, and an ancillary treatment system 260. The treatment device 220 is further comprised of a chamber 221 having an opening 223 at one end, which is sealed using sealing means that are described in more detail below. In the illustrated embodiment, the finger 212 of a patient extends through the opening 223 so that the finger 212 may be treated with reduced pressure by the appliance 210. The vacuum system 230 is generally comprised of a reduced pressure supply source, illustrated schematically and generally designated 231, and reduced pressure supply means 232 that operably connect the reduced pressure supply source 231 to the chamber 221 so that reduced pressure is supplied to the volume within the chamber 221 at the portion of the body (finger 212) to be treated. In the various embodiments of this second version of the present invention, the vacuum system 230 may have substantially the same structure, features, characteristics and operation as the embodiments of the vacuum system 30 described above and illustrated in connection with FIG. 1. In other embodiments, the vacuum system 230 may be comprised of a suction bulb system, which is illustrated in FIG. 8 and described in more detail below. The ancillary treatment system 260 is generally comprised of a treatment supply source, illustrated schematically and generally designated 261, and treatment supply means 262 that operably connect the treatment supply source 261 to the chamber 221 so that various treatments may be supplied to the volume within the chamber 221 at the portion of the body (finger 212) to be treated. In the various embodiments of this second version of the present invention, the ancillary treatment system 260 may have substantially the same structure, features, characteristics and operation as the embodiments of the treatment port 28 or the forced entry treatment system 60, or both, described above and illustrated in connection with FIG. 1. It is to be noted that in some embodiments there may be more than one ancillary treatment system 260 or more than one treatment supply means 262, and in other embodiments there may not be any treatment system 260. The chamber 221 is generally adapted to be of a size and shape to fit over and enclose all or a portion of a distal extremity (i.e., finger or toe) of a patient. The chamber 221 is also generally constructed of a rigid or semi-rigid material that is rigid enough to generally support the chamber 221 away from the portion of the distal extremity (finger 212) to be treated by the appliance 210, although there may be some contact between such portion 212 and the interior surface of the chamber 221. For example, the chamber 221 may be constructed of woods, metals, glasses, ceramics, plastics, or other rigid or semi-rigid polymers (such as polyvinyl chloride or polycarbonate) or combinations of such materials. Although the opening 223 of the chamber 221 in the illustrated embodiment is approximately circular in shape, the opening 223 may be of almost any size or shape, as long as it does not interfere with the operation of the chamber 221 and permits the distal extremity (the finger 212 in FIG. 7) to be treated to be positioned within the volume of the chamber 221. In the illustrated embodiment, the sealing means 224 is comprised of a flexible sleeve 224 that has substantially the same structure, features, characteristics and operation as the embodiments of the flexible sleeve 24 described above and illustrated in connection with FIG. 1. In other embodiments, the sealing means 224 may be comprised of substantially the same structure, features, characteristics and operation as any of the embodiments of the sealing means 24 described above and illustrated in connection with FIG. 1, to the extent that such sealing means 24 applies to treatment of only a portion of an object. In addition, the sealing means 224 may be comprised of the shape of the opening 223 being approximately the same size and shape as the portion of the body that is adjacent to the opening 223, wherein the chamber 221 is held against such adjacent portion of the body using an adhesive, adhesive tape, lubricating material (such as lanoline), or the reduced pressure within the chamber 221.

An embodiment of a suction bulb system that may be used with embodiments of the present invention is illustrated in FIG. 8. In this embodiment, the vacuum system 230 is generally comprised of a suction bulb 271 having an inlet port 272 and an outlet port 273, a bulb connection tubing member 274, an exhaust tubing member 275, an exhaust control valve 276, a filter 277, and a supplemental vacuum system (illustrated schematically and generally designated 230a). In this embodiment, the suction bulb 271 is a hollow sphere that may be used to produce a supply of reduced pressure for use with the treatment device 220. In addition, the suction bulb 271 may also be used to receive and store fluid aspirated from the distal extremity 212. The inlet port 272 of the suction bulb 271 is connected to one end of the bulb connection tubing member 274, which is also the reduced pressure supply means 232 in this embodiment. The connection tubing member 274 is connected to the chamber 221 by a port 225 in a manner so that the interior volume of the suction bulb 271 is in fluid communication with the volume within the chamber 221. In this embodiment, the bulb connection tubing member 274 is sufficiently flexible to permit movement of the bulb connection tubing member 274, but is sufficiently rigid to resist constriction when reduced pressure is supplied to the chamber 221. The outlet port 273 of the suction bulb 271 is connected to the exhaust tubing member 275. In this embodiment, the exhaust tubing member 275 is sufficiently flexible to permit movement of the exhaust tubing member 275, but is sufficiently rigid to resist constriction when reduced pressure is supplied to the chamber 221. The inlet port 272 of the suction bulb 271 may be connected to the bulb connection tubing member 274 and the outlet port 273 of the suction bulb 271 may be connected to the exhaust tubing member 275 using any suitable means, such as by welding, fusing, adhesives, clamps, or any combination of such means. In addition, in some embodiments, which are the preferred embodiments, the suction bulb 271, the bulb connection tubing member 274, and the exhaust tubing member 275 may be fabricated as a single piece. In the illustrated embodiment, the exhaust control valve 276 and the filter 277 are operably connected to the exhaust tubing member 275. In this embodiment, the exhaust control valve 276 is used to regulate the flow of fluids (gases and liquids) to and from the suction bulb 271 and the supplemental vacuum system 230a. In embodiments of the invention that do not have a supplemental vacuum system 230a, the exhaust control valve 276 regulates flow of fluids to and from the suction bulb 271 and the outside atmosphere. Generally, the exhaust control valve 276 allows fluids to flow out of the suction bulb 271 through the outlet port 273, but not to flow in the reverse direction unless permitted by the user of the appliance 210. Any type of flow control valve may be used as the exhaust control valve 276, as long as the valve 276 is capable of operating in the anticipated environment involving reduced pressure and exudate. Such valves are well known in the relevant art, such as sprung and unsprung flapper-type valves and disc-type valves, operating in conjunction with or without ball, gate and other similar types of valves. In this embodiment, the filter 277 is operably attached to the exhaust tubing member 275 between the outlet port 273 of the suction bulb 271 and the exhaust control valve 276. The filter 277 prevents potentially pathogenic microbes or aerosols from contaminating the exhaust control valve 276 (and supplemental vacuum system 230a), and then being vented to atmosphere. The filter 277 may be any suitable type of filter, such as a micropore filter. In other embodiments, the filter 277 may also be a hydrophobic filter that prevents any exudate from the portion of the distal extremity (finger 212) from contaminating the exhaust control valve 276 (and the supplemental vacuum system 230a) and then being vented to atmosphere. In still other embodiments, the filter 277 may perform both functions. It is to be noted, however, that the outlet port 273, the exhaust control valve 276, the filter 277, or any combination of the exhaust control valve 276 and the filter 277, need not be utilized in connection with the vacuum system 230 in other embodiments of the invention.

In some embodiments of the present invention that do not utilize a supplemental vacuum system 230a, the suction bulb 271 may be used to produce a supply of reduced pressure in the following manner. First, the user of the appliance 210 appropriately seals all of the component parts of the appliance 210 in the manner described herein. For example, the chamber 221 is placed over and encloses the portion 212 of the body to be treated, and the opening 223 of the chamber 221 is sealed using the sealing means 224. The user then opens the exhaust control valve 276 and applies force to the outside surface of the suction bulb 271, deforming it in a manner that causes its interior volume to be reduced. When the suction bulb 271 is deformed, the gas in the interior volume is expelled to atmosphere through the outlet port 273, the exhaust tubing member 275, the filter 277, and the exhaust control valve 276. The user then closes the exhaust control valve 276 and releases the force on the suction bulb 271. The suction bulb 271 then expands, drawing fluid (liquid and gas) from the volume within the treatment device 220 into the suction bulb 271 through the bulb connection tubing member 274 and causing the pressure in such volume to decrease. To release the reduced pressure, the user of the appliance 210 may open the exhaust control valve 276, allowing atmospheric air into the interior volume of the suction bulb 271. The level of reduced pressure may also be regulated by momentarily opening the exhaust control valve 276.

The suction bulb 271 may be constructed of almost any suitable fluid impermeable flexible or semi-rigid material that can be readily deformed by application of pressure to the outside surface of the suction bulb 271 by users of the appliance 270 and still return to its original shape upon release of the pressure. For example, the suction bulb 271 may be constructed of rubber, neoprene, silicone, or other flexible or semi-rigid polymers, or any combination of all such materials. In addition, the suction bulb 271 may be of almost any shape, such as cubical, ellipsoidal, or polygonal. The suction bulb 271 may also be of varying size depending upon the anticipated use of the suction bulb 271, the size of the treatment device 220, use of a supplemental vacuum system 230a, the level of reduced pressure desired, and the preference of the user of the appliance 210. In the embodiment of the invention illustrated in FIG. 8, the supplemental vacuum system 230a is connected to the exhaust tubing member 275 and is used to provide a supplemental supply of reduced pressure to the suction bulb 271 and treatment device 220. In this embodiment, the supplemental vacuum system 230a may have substantially the same structure, features, characteristics and operation of the various embodiments of the vacuum system 30 of the first version of the invention described above and illustrated in connection with FIG. 1. It is to be noted, however, that the supplemental vacuum system 230a need not be used in connection with the vacuum system 230 in other embodiments of the invention.

The present invention also includes a method of administering reduced pressure treatment to a distal extremity using various embodiments of the second version of the present invention, as described above and illustrated in connection with FIG. 7. Generally, the method comprises the following steps. First, an appliance 210 for administering reduced pressure to the distal extremity (the finger 212 in FIG. 7) is provided. Second, the appliance 210 is placed over the portion of the distal extremity to be treated (the finger 212 in FIG. 5), so that the chamber 221 encloses the portion of the finger 212 to be treated. Third, the opening 223 of the chamber 221 is sealed using the sealing means (the flexible sleeve 224 in FIG. 7), so that reduced pressure may be maintained in the volume within the chamber 221. Fourth, the chamber 221 is operably connected with the reduced pressure supply source 231 using the reduced pressure supply means 232 so that reduced pressure is supplied to the volume within the chamber 221. It is to be noted that the fourth step may be also performed before either the second or third step described above. In the preferred embodiments of this second version of the invention, the reduced pressure maintained in the volume within the chamber 221 at the portion of the distal extremity to be treated (the finger 212 in FIG. 7) is in the range from approximately 20 mm of Hg below atmospheric pressure to approximately 125 mm of Hg below atmospheric pressure. In yet other embodiments, the reduced pressure is applied to the chamber 221 in a cyclic nature, the cyclic nature providing alternating time periods of application of reduced pressure and non-application of reduced pressure. Fifth, the reduced pressure is maintained in the volume within the chamber 221 until the portion of the distal extremity being treated (the finger 212 in FIG. 7) has progressed toward a selected stage of treatment. In embodiments comprising an ancillary treatment system 260, the method also includes the step of positioning the treatment supply source 261 in proximity to the treatment device 220, connecting the treatment supply means 262 to the treatment supply source 261 and the chamber 221, and operating the ancillary treatment system 260 until the desired treatment is completed.

Figure 9:
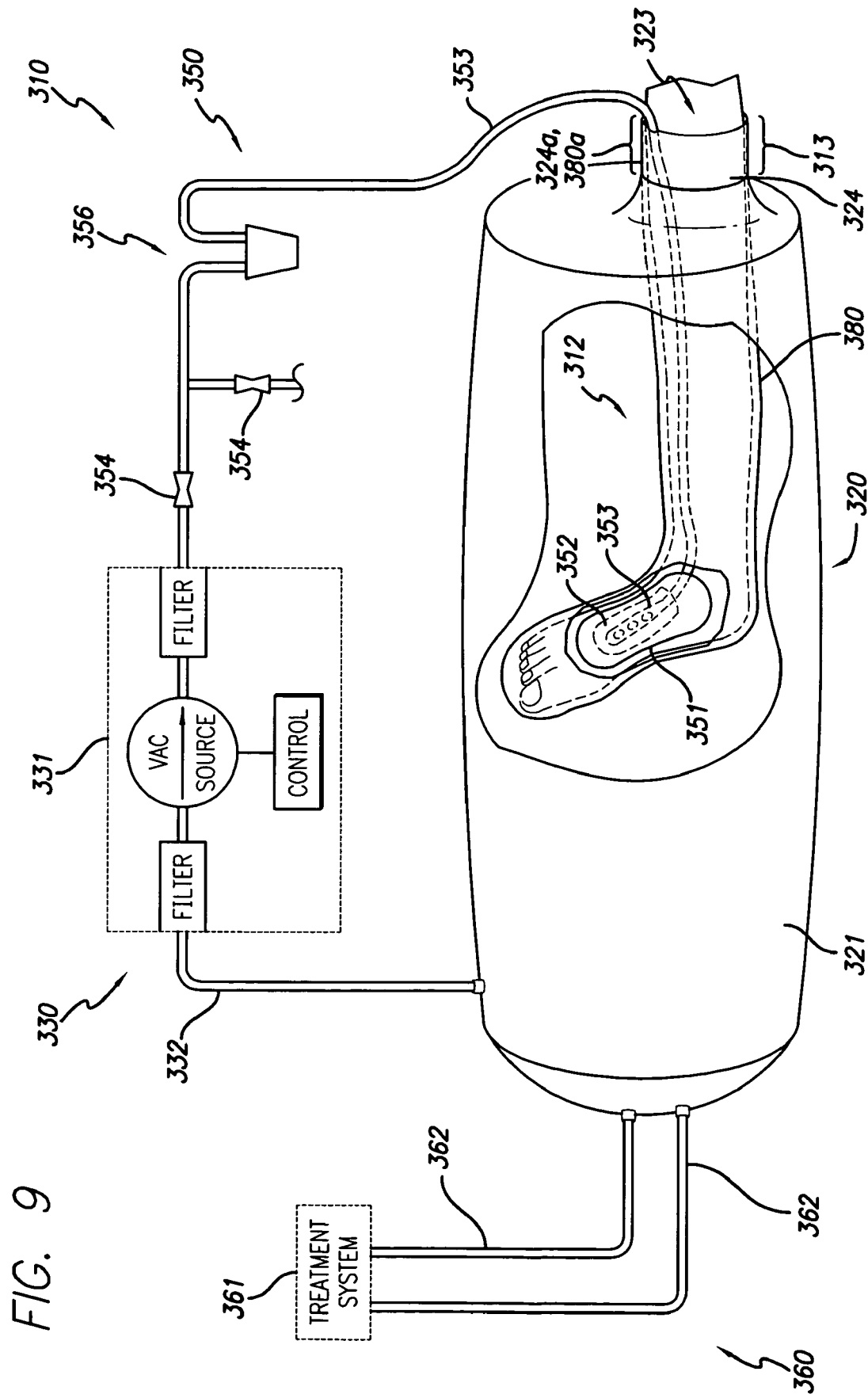
FIG. 9 is a view of an appliance comprising the present invention, in which an embodiment of a treatment device, shown in partially broken-away perspective view, encloses the lower leg portion of a patient, and in which embodiments of a vacuum system and a forced entry treatment system, depicted generally and shown in schematic elevation view, provide reduced pressure and various treatment means, respectively, to the treatment device.

An embodiment of a third version of the present invention is illustrated in FIG. 9. In this embodiment, the present invention includes an appliance 310 that is generally comprised of a treatment device 320, a vacuum system 330, a drainage system 350, and a forced entry treatment system 360. In this embodiment, the treatment device 320 is further comprised of a chamber 321 having an opening 323, sealing means (a flexible sleeve 324 in FIG. 7) to seal the opening 323 so that reduced pressure may be maintained in the volume within the chamber 321, and a liner 380. In the illustrated embodiment, the liner 380 is positioned over the portion of the body 312 to be treated, which extends through the opening 323 so that the portion 312 may be treated with reduced pressure by the appliance 310. The vacuum system 330 is generally comprised of a reduced pressure supply source, illustrated schematically and generally designated 331, and reduced pressure supply means 332 that operably connect the reduced pressure supply source 331 to the chamber 321 so that reduced pressure is supplied to the volume within the chamber 321 at the portion of the body 312 to be treated. In the various embodiments of this third version of the present invention, the vacuum system 330 may have substantially the same structure, features, characteristics and operation as the embodiments of the vacuum system 30 described above and illustrated in connection with FIG. 1. The forced entry treatment system 360 is generally comprised of a forced entry supply source, illustrated schematically and generally designated 361, and forced entry supply means 362 that operably connect the forced entry supply source 361 to the chamber 321 so that various treatments may be supplied to the volume within the chamber 321 at the portion of the body 312 to be treated. In the various embodiments of this third version of the present invention, the forced entry treatment system 360 may have substantially the same structure, features, characteristics and operation as the embodiments of the forced entry treatment system 60 described above and illustrated in connection with FIG. 1. It is to be noted that in some embodiments there may be more than one forced entry treatment system 360 and in other embodiments there may not be any forced entry treatment system 360. The drainage system 350 may be generally comprised of combinations of an overlay 351, wound packing means 352, draining means 353, valves 354, and collection system 356. In the various embodiments of this third version of the present invention, the drainage system 350 may have substantially the same structure, features, characteristics and operation as the embodiments of the drainage system 50 described above and illustrated in connection with FIG. 1. It is to be noted that in some embodiments there may be more than one drainage system 350 and in other embodiments there may not be any drainage system 350. In yet other embodiments, the drainage system 350 may contain all of the components of the illustrated drainage system 350, while in still other embodiments the drainage system 350 may contain only some of the components.

In some embodiments of this third version of the present invention, the chamber 321 may have substantially the same structure, features, characteristics and operation as the embodiments of the flexible chamber 21 and its supporting collapsible frame 22 described above and illustrated in connection with FIG. 1. In other embodiments, the chamber 321 may have a different structure, shape or size. For example, the chamber 321 may be comprised of a rigid or semi-rigid material and may have a rectangular cross-sectional shape. In addition, the sealing means 324 utilized in the various embodiments of this third version of the present invention may generally be comprised of any of the sealing means 24 described above and illustrated in connection with FIG. 1. The liner 380 is generally adapted to be of a size and shape to cover the portion 312 of the body to be treated, as well as an additional portion 313 of the body that extents to at least the sealing portion 324a of the flexible sleeve 324. Thus, in this version of the invention, the sealing means (the flexible sleeve 324) may be sealed against the liner 380 rather than the portion 313 of the body adjacent to the sealing portion 324a of the flexible sleeve 324. This seal may provide for permanent attachment, or for removable attachment, and seal of the liner 380 to the flexible sleeve 324. The portion 313 of the body that is approximately adjacent to the sealing portion of the liner 380a is also sealed in a manner so that reduced pressure may be maintained in the volume within the chamber 321. Such sealing means may be comprised of any suitable means, such as adhesives, adhesive tapes, the reduced pressure within the chamber 321, or other means or combinations of such means. The liner 380 is generally comprised of a material that is impermeable or semi-permeable with respect to fluids (liquids and gases). Where semi-permeable materials are used, the reduced pressure within the chamber 321 is also applied to the portion of the body 312 enclosed by the liner 380, but any exudate aspirated from such portion 312 of the body is generally not able to pass through the liner 380 to the interior volume of the chamber 321. For example, the liner 380 may be constructed of polyurethane or other semi-permeable polymers (such as that sold by the 3M Corporation under the trademark IOBAN), or combinations of such materials. This enables the application of reduced pressure to the portion 312 of the body to be treated, without contamination of the chamber 321 by any exudate aspirated from the portion 312 of the body to be treated. It is to be noted that the liner 380 may be used in other embodiments of this third version of the present invention with or without an overlay 351, draining means 353, or wound packing means 352. The method of using the embodiments of this third version of the invention is substantially similar to the method used to operate the embodiments of the first version of the present invention described above and illustrated in connection with FIG. 1, except that this version includes the steps of placing the portion 312 of the body to be treated into the liner 380, sealing the liner 380 to the portion 313 of the body adjacent to the sealing portion 380a of the liner 380, and where necessary, sealing the flexible sleeve 324 to the liner 380.

What is claimed is:

1. An appliance for administering reduced pressure treatment to an object or a portion of an object, the appliance comprising:
    a flexible chamber having an opening, wherein the flexible chamber is sized to enclose substantially all of the object or the portion of the object to be treated and adapted to maintain reduced pressure within the volume of the flexible chamber, wherein the chamber is a single chamber, said object or portion of the object extending through the opening into the volume defined by the flexible chamber;
    a collapsible frame, wherein the collapsible frame supports the flexible chamber away from the object or the portion of the object to be treated while the appliance is in use, and wherein the collapsible frame comprises one or more longitudinal frame members extending longitudinally along the length of the chamber and one or more circumferential frame members extending circumferentially across the chamber generally transverse to a longitudinal axis of the chamber, at least one of the one or more longitudinal members being movable between a collapsed configuration and an extended configuration, and wherein the longitudinal and circumferential frame members are inflatable and are in fluid communication with each other;
    a sealing mechanism to seal the opening so that reduced pressure may be maintained within the volume of the flexible chamber; and
    a reduced pressure supply mechanism to operably connect the flexible chamber to a reduced pressure supply source that provides a supply of reduced pressure to the flexible chamber, so that the volume within the flexible chamber is supplied with reduced pressure by the reduced pressure supply source in an amount sufficient to treat a wound, and wherein the chamber has a substantially uniform pressure throughout the volume defined by the flexible chamber;
    wherein the flexible chamber and the collapsible frame may be collapsed to a smaller size when the appliance is not in use.

2. The appliance of claim 1, wherein: the one or more longitudinal frame members and the one or more circumferential frame members of the collapsible frame comprise at least one inflatable member, wherein the at least one inflatable member is inflated with a pressurized fluid when the appliance is in use and may be deflated when the appliance is not in use; and the appliance is further comprised of a pressurized fluid supply source and pressurized fluid supply mechanism to operably connect the collapsible frame to the pressurized fluid supply source, so that the at least one inflatable member is supplied with the pressurized fluid by the pressurized fluid supply source.

3. The appliance of claim 2, wherein the one or more longitudinal frame members and the one or more circumferential frame members of the collapsible frame comprise at least two inflatable members and the at least two inflatable members are operably connected together so that the pressurized fluid may flow between them.

4. The appliance of claim 2, wherein the pressurized fluid is compressed air and the pressurized fluid supply source is an air compressor.

5. The appliance of claim 2, wherein the sealing mechanism is comprised of a flexible sleeve.

6. The appliance of claim 1, wherein the flexible chamber is comprised of a flexible or semi-flexible polymer material.

7. The appliance of claim 1, wherein the reduced pressure supply source is comprised of a vacuum pump.

8. The appliance of claim 7, wherein the reduced pressure supply source further comprises a control system for the vacuum pump, wherein the control system controls the operation of the vacuum pump.

9. The appliance of claim 7, wherein: the reduced pressure supply source further comprises a filter operably positioned between the vacuum pump and the reduced pressure supply mechanism; and the filter prevents the venting of and contamination of the vacuum pump by micro-organisms or fluids or both aspirated from the portion of the body to be treated.

10. The appliance of claim 1, wherein the reduced pressure supply mechanism is comprised of flexible tubing.

11. The appliance of claim 1, wherein the reduced pressure supply mechanism is further comprised of a suction bulb system.

12. The appliance of claim 1, wherein the reduced pressure within the volume of the flexible chamber in the area of the portion of the body to be treated is in the range from approximately 20 mm of Hg below atmospheric pressure to approximately 125 mm of Hg below atmospheric pressure.

13. The appliance of claim 1, wherein the reduced pressure is applied in a cyclic nature, the cyclic nature providing alternating time periods of application of reduced pressure and without application of reduced pressure.

14. The appliance of claim 1, wherein the treatment device further comprises a treatment port operably attached to the flexible chamber and the treatment port permits fluids and other instrumentalities to be introduced into the volume within the flexible chamber.

15. The appliance of claim 1, wherein the treatment device further comprises a forced entry treatment system operably connected to the flexible chamber for introducing ancillary fluids into the volume within the flexible chamber.

16. The appliance of claim 1, wherein the appliance further comprises a drainage system operably disposed between the flexible chamber and the portion of the body to be treated.

17. The appliance of claim 16, wherein the drainage system further comprises: an overlay, wherein the overlay is sized to be placed over and enclose a part of the portion of the body to be treated; and an overlay sealing mechanism to operably seal the overlay to the body.

18. The appliance of claim 17, wherein the overlay is comprised of a semi-permeable material, so that reduced pressure may be maintained in the volume under the overlay at said part of the body.

19. The appliance of claim 17, wherein the drainage system further comprises a draining mechanism extending from the volume under the overlay at said part of the body to an area outside the volume of the flexible chamber so that exudate aspirated from said part of the body may be drained from said part of the body to such outside area.

20. The appliance of claim 19, wherein the area outside the volume of the flexible chamber is the reduced pressure supply source, so that the draining mechanism is in fluid communication with the reduced pressure supply source and reduced pressure is supplied by the draining mechanism to the volume under the overlay at said part of the body.

21. The appliance of claim 20, wherein the draining mechanism is further comprised of a collection system that is operably positioned between the overlay and the reduced pressure supply source and the collection system comprises a container to receive and hold fluid aspirated from said part of the body.

22. The appliance of claim 21, wherein the collection system is further comprised of a pressure halting mechanism to halt the application of reduced pressure to the volume under the overlay at said part of the body when the fluid in the container exceeds a predetermined amount.

23. The appliance of claim 17, wherein the drainage system further comprises a wound packing mechanism disposed between the overlay and said part of the body.

24. The appliance of claim 1, further comprising a fluid impermeable or semi-permeable liner disposed between the chamber and the portion of the body positioned within the chamber.

25. The appliance of claim 24, further comprising a sealing mechanism to seal the fluid impermeable or semi-permeable liner to the portion of the body positioned within the chamber, so that reduced pressure may be maintained within the volume of the chamber and the volume of the liner.

26. The appliance of claim 1, wherein at least one of the one or more longitudinal frame members is disposed axially between two circumferential frame members.

27. An appliance for administering reduced pressure treatment to an object or a portion of an object, the appliance comprising:
a flexible chamber having an opening, wherein the flexible chamber is sized to enclose substantially all of the object or the portion of the object to be treated and adapted to maintain reduced pressure within the volume of the flexible chamber, wherein the chamber is a single chamber, said object or portion of the object extending through the opening into the volume defined by the flexible chamber;
a collapsible frame, wherein the collapsible frame supports the flexible chamber away from the object or the portion of the object to be treated while the appliance is in use, and wherein the collapsible frame comprises one or more longitudinal frame members extending longitudinally along the length of the chamber and one or more circumferential frame members extending circumferentially across the chamber generally transverse to a longitudinal axis of the chamber, at least one of the one or more longitudinal members being movable between a collapsed configuration and an extended configuration;
a sealing mechanism to seal the opening so that reduced pressure may be maintained within the volume of the flexible chamber; and
a reduced pressure supply mechanism to operably connect the flexible chamber to a reduced pressure supply source that provides a supply of reduced pressure to the flexible chamber, so that the volume within the flexible chamber is supplied with reduced pressure by the reduced pressure supply source in an amount sufficient to treat a wound, and wherein the chamber has a substantially uniform pressure throughout the volume defined by the flexible chamber;
wherein the flexible chamber and the collapsible frame may be collapsed to a smaller size when the appliance is not in use, and wherein the one or more longitudinal frame members and the one or more circumferential frame members of the collapsible frame comprise at least one inflatable member, wherein the at least one inflatable member is inflated with a pressurized fluid when the appliance is in use and may be deflated when the appliance is not in use; and the appliance is further comprised of a pressurized fluid supply source and pressurized fluid supply mechanism to operably connect the collapsible frame to the pressurized fluid supply source, so that the at least one inflatable member is supplied with the pressurized fluid by the pressurized fluid supply source.

28. The appliance of claim 27, wherein the flexible chamber comprises a flexible or semi-flexible polymer material.

29. The appliance of claim 27, wherein the reduced pressure supply source comprises a vacuum pump.

30. The appliance of claim 29, wherein the reduced pressure supply source further comprises a control system for the vacuum pump, wherein the control system controls the operation of the vacuum pump.

31. The appliance of claim 29, wherein: the reduced pressure supply source further comprises a filter operably positioned between the vacuum pump and the reduced pressure supply mechanism; and the filter prevents the venting of and contamination of the vacuum pump by micro-organisms or fluids or both aspirated from the portion of the body to be treated.

32. The appliance of claim 27, wherein the appliance further comprises a drainage system operably disposed between the flexible chamber and the portion of the body to be treated.

33. The appliance of claim 32, wherein the drainage system further comprises: an overlay, wherein the overlay is sized to be placed over and enclose a part of the portion of the body to be treated; and an overlay sealing mechanism to operably seal the overlay to the body.

34. The appliance of claim 33, wherein the drainage system further comprises a wound packing mechanism disposed between the overlay and said part of the body.

35. The appliance of claim 27, further comprising a fluid impermeable or semi-permeable liner disposed between the chamber and the portion of the body positioned within the chamber.

36. The appliance of claim 35, further comprising a sealing mechanism to seal the fluid impermeable or semi-permeable liner to the portion of the body positioned within the chamber, so that reduced pressure may be maintained within the volume of the chamber and the volume of the liner.

\* \* \* \* \*